(12) United States Patent
Hrkach

(10) Patent No.: US 8,887,715 B2
(45) Date of Patent: *Nov. 18, 2014

(54) LOW DOSE PHARMACEUTICAL POWDERS FOR INHALATION

(71) Applicant: Civitas Therapeutics, Inc., Chelsea, MA (US)

(72) Inventor: Jeffrey S. Hrkach, Lexington, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,315

(22) Filed: May 2, 2013

(65) Prior Publication Data

US 2013/0306069 A1    Nov. 21, 2013

Related U.S. Application Data

(60) Continuation of application No. 13/096,475, filed on Apr. 28, 2011, now Pat. No. 8,454,939, which is a division of application No. 10/867,375, filed on Jun. 14, 2004, now Pat. No. 7,954,491.

(60) Provisional application No. 60/478,315, filed on Jun. 13, 2003.

(51) Int. Cl.
*A61M 15/00* (2006.01)
*A61K 9/00* (2006.01)

(52) U.S. Cl.
CPC .......... *A61M 15/0028* (2013.01); *A61K 9/0075* (2013.01); *A61M 2209/02* (2013.01); *A61M 15/0091* (2013.01); *A61M 15/0035* (2013.01); *A61M 2202/064* (2013.01); *A61M 2206/16* (2013.01)

USPC .................. 128/200.24; 128/203.15; 424/46; 424/489

(58) Field of Classification Search
USPC ............ 128/200.23, 200.14, 203.14, 203.15, 128/725, 200.24, 200.2; 424/46, 489
See application file for complete search history.

(56) References Cited

U.S. PATENT DOCUMENTS 6,613,308 B2 *  9/2003  Bartus et al. .................... 424/45
6,766,799 B2 *  7/2004  Edwards et al. ......... 128/203.15

(Continued)

FOREIGN PATENT DOCUMENTS

WO    0195874 A2    12/2001
WO    0224158 A2     3/2002

(Continued)

OTHER PUBLICATIONS

Coskun et al., Standard dose of inhaled albuterol significantly increases QT dispersion compared to low dose of albuterol plus ipratropium bromide therapy in moderate to severe acute asthma attacks in children; 2001; Pediatrics International, 43:631-636.*

(Continued)

*Primary Examiner* — Jane C Oswecki
(74) *Attorney, Agent, or Firm* — Darlene A. Vanstone; Carolyn S. Elmore; Elmore Patent Law Group, P.C.

(57) ABSTRACT

The invention relates to a method of delivering an agent to the pulmonary system of a compromised patient, in a single breath-activated step, comprising administering a particle mass comprising an agent from an inhaler containing less than 5 milligrams of the mass, wherein at least about 50% of the mass in the receptacle is delivered to the pulmonary system of a patient. The invention also relates to receptacles containing the particle mass and the inhaler for use therein.

17 Claims, 20 Drawing Sheets

(56) References Cited

U.S. PATENT DOCUMENTS

| | | | |
|---|---|---|---|
| 7,556,798 B2 * | 7/2009 | Edwards et al. | 424/45 |
| 7,954,491 B2 * | 6/2011 | Hrkach | 128/203.15 |
| 8,454,939 B2 * | 6/2013 | Hrkach | 424/46 |

FOREIGN PATENT DOCUMENTS

| | | |
|---|---|---|
| WO | 02083220 A2 | 10/2002 |
| WO | 03080163 A1 | 10/2003 |

OTHER PUBLICATIONS

Cipolla et al., Bolus Administration of INS365: Studying the Feasibility of Delivering High Dose Drugs Using the AERx(R) Pulmonary Delivery System; 2000; Respiratory Drug Delivery VII; pp. 231-239.*

* cited by examiner

LOW DOSE PHARMACEUTICAL POWDERS FOR INHALATION

RELATED APPLICATION

This application is a continuation of U.S. application Ser. No. 13/096,475, filed Apr. 28, 2011, which is a divisional of U.S. application Ser. No. 10/867,375, filed Jun. 14, 2004, now U.S. Pat. No. 7,954,491, which claims the benefit of U.S. Provisional Application No. 60/478,315, filed on Jun. 13, 2003. The entire teachings of the above applications are incorporated herein by reference.

BACKGROUND OF THE INVENTION

Inhalation of aerosol powders from dry powder inhalers (DPI's) is a convenient way of delivering drugs to patients, such as asthmatics. Current DPI's typically make use of small amounts of micronized drug blended with large amounts of carrier particles, such as a lactose carrier, to facilitate efficient delivery of the drug to the lungs. The efficiency and reproducibility of delivery of such blends is dependent on the patient's lung function and can be effected by parameters such as inspiratory flow rate and/or volume. Existing DPI's can be reservoir based, such as those capable of storing and delivering large numbers of doses to patients, as well as receptacle based, such as those utilizing capsules or blisters.

Patients that could benefit from drugs delivered via a DPI often times do have compromised or reduced lung function, which can alter, reduce, or delay the efficiency of delivery or therapeutic onset of the drug. Conditions leading to such compromised lung function include asthma, COPD, anaphylaxis, emphysema, and other forms of respiratory distress. Other factors such as a patient's age (i.e. children or elderly patients), history (i.e. smoking, chemical exposure) and other conditions can also lead to a reduction of inspiratory flow rate and/or volume.

A need exists to be able to efficiently and reproducibly deliver therapeutic agents to the lungs of such compromised patients. This would optimally utilize low masses of dry particles capable of being delivered via a single breath-activated step, especially at low inspiratory flow rates and/or low inspiratory volumes. Also, a need exists to deliver a large fraction of the mass of such particles from the DPI to the pulmonary system of a compromised patient.

SUMMARY OF THE INVENTION

It is therefore an object of the invention to deliver an effective amount of therapeutic, prophylactic or diagnostic agents by dry powder aerosols without the need for particle levels typically found with capsule-based delivery systems, such as those including a carrier.

It is therefore an object of the invention to deliver an effective amount of therapeutic, prophylactic or diagnostic agents by dry powder aerosols having lower dose levels, for example, less than 5 mg.

It is another object of the invention to deliver an effective amount of therapeutic, prophylactic or diagnostic agents by dry powder aerosols having lower dose levels, for example, less than 5 mg to compromised patients having low inspiratory flow rates of less than 20 L/minute.

It is another object of the invention to deliver a dry powder aerosol with a respirable fraction (<4.7 µm) of 45% or more which maintains a high emitted dose over a very broad flow rate range, such as between 15-60 L/min.

The invention relates to a method of delivering an agent to the pulmonary system of a compromised patient, in a single breath-activated step, comprising administering a particle mass comprising an agent from an inhaler containing less than 5 milligrams of the mass, wherein at least about 50% of the mass in the receptacle is delivered to the pulmonary system of the patient.

In another embodiment, the invention relates to a receptacle containing less than 5 milligrams of particle mass comprising an agent wherein, upon delivery to the pulmonary system of a compromised patient, in a single breath-activated step, at least about 50% of the mass in the receptacle is delivered to the pulmonary system of the patient.

Further, the invention relates to an inhaler for use in a method for delivering an agent to the pulmonary system of a compromised patient, in a single breath-activated step comprising administering a particle mass comprising an agent from an inhaler containing less than 5 milligrams of the mass, wherein at least about 50% of the mass in the receptacle is delivered to the pulmonary system of the patient.

BRIEF DESCRIPTION OF THE FIGURES

The present invention is described with reference to the accompanying drawings.

In the drawings, like reference numbers indicate identical or functionally similar elements.

DETAILED DESCRIPTION

Figure 1:
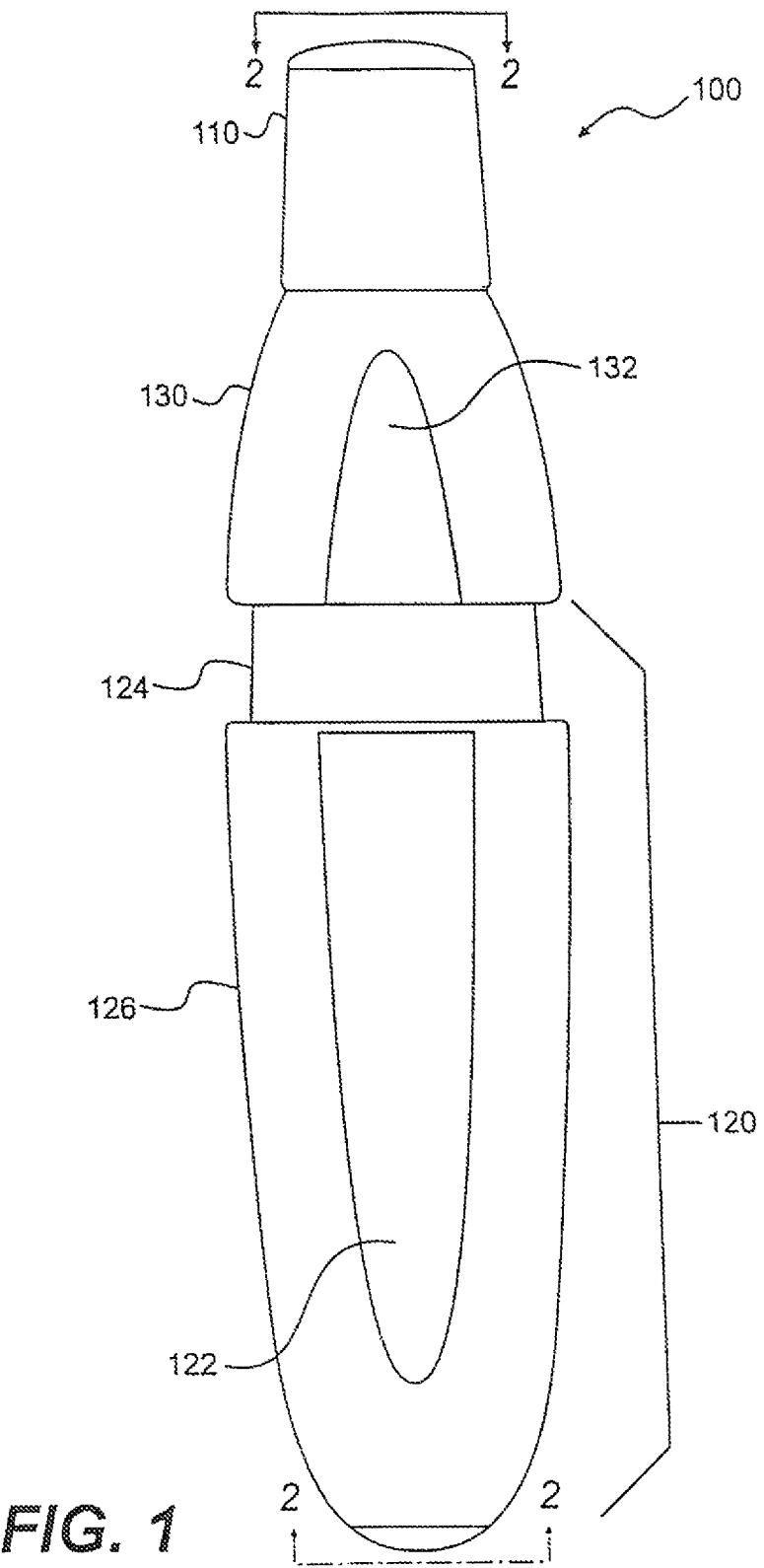
FIG. 1 is a front view of one embodiment of a device of the present invention.

The invention relates to a method of delivering an agent to the pulmonary system of a compromised patient, in a single breath-activated step, comprising administering a particle mass comprising an agent from an inhaler containing less than 5 milligrams of the mass, wherein at least about 50% of the mass in the receptacle is delivered to the pulmonary system of the patient.

Applicants have been improving methods of delivering particle masses, in particular, dry particles for oral delivery. Applicant have discovered methods to deliver an effective amount of therapeutic, prophylactic or diagnostic agents by dry particles aerosols having lower dose levels, for example, less than 5 mg, in particular, in the range of 3 mg to 5 mg. Until the present invention, it has been a challenge to administer aerosols having lower dose levels, for example, less than 5 mg to compromised patients having low inspiratory flow rates, for example, less than 20 L/minute. Applicant have been able to deliver a chemically stable dry particle aerosol with a respirable fraction (<4.7 μm) of 45% which maintains a high emitted dose (>80%) over a flow rate range of 15-60 L/min, that is, over a range of inhalation flow rates.

Compromised patients include individuals who do not or cannot breathe hard or have a compromised lung function. Examples of such individuals include children, including growth hormone deficient children, elderly persons, persons suffering from respiratory disease, such as conditions leading to such compromised lung function include asthma, COPD, anaphylaxis, emphysema, and other forms of respiratory distress. Other factors such as a patient's age (i.e. children or elderly patients), history (i.e. smoking, chemical exposure) and other conditions can also lead to a reduction of inspiratory flow rate and/or volume. Other individuals include sleeping individuals and comatose individuals. Preferably, the individuals are vertical during the method. However, it is also possible to practice the method horizontally. Preferably, human growth hormone is administered to children at doses of less than 5 mg, such as less than 4 mg.

Generally, the individual will have a peak inspiratory flow rate (PIFR) of less than about 20 liters per minute. In one embodiment, the patient will have a PIFR of about 15 liters per minute or less. Alternatively or additionally, the compromised patient has an inspiration volume of less than 2 liters, such as less than 1.5 liters, including less than 1 liter, such as 0.75 liters.

The method is particularly useful in delivering agents that are useful in treating the cause of the patient's compromised state, such as administering epinephrine for treating or preventing anaphylaxis, growth hormone for growth hormone deficient children, or asthma medications, such as albuterol, fluticasone formoterol, ipatroium bromide, trospium chloride or salmeterol, for treating asthma.

A particular advantage of the invention rests in the discovery that delivery of very small amounts of drug (e.g. particle mass) can be achieved independently of PIFR. This unexpected discovery permits reliable and reproducible dosing for the patient, irrespective of the patient's particular condition and the need to determine the patient's actual flow rate prior to administering the dose, even at very low doses of particle mass.

Thus, in a preferred embodiment, the inhaler, or the receptacle which may be disposed within the inhaler, contains less than 4 milligrams of the particle mass, preferably less than about 3 milligrams (such as about 3.4 mg). In one embodiment, the mass of particles contains epinephrine at a dose of about 250 to 750 micrograms of epinephrine.

The particle mass is highly dispersible and possesses good to excellent deposition in the lung. Examples of preferred particle masses possess a tap density of less than about 0.4 $g/cm^3$, preferably less than about 0.1 $g/cm^3$, such as less than about 0.05 $g/cm^3$. Tap density is a measure of the envelope mass density characterizing a particle. The envelope mass density of particles of a statistically isotropic shape is defined as the mass of the particle divided by the minimum sphere envelope volume within which it can be enclosed.

Preferred particle masses possess a mass mean geometric diameter of the mass, as emitted from the inhaler, between about 1 micron and 20 microns, such as between about 3 and 15 microns, more preferably between about 3 microns and 10 microns. Good deposition to the lung can be achieved with particle masses possessing a preferred mass mean aerodynamic diameter of the mass emitted from the inhaler is between about 1 to 5 microns, such as between about 1 and 3 microns. Preferred particles masses include or consist of spray-dried particles.

Features that can contribute to low tap density, large geometric diameter and low aerodynamic diameter include irregular surface texture and hollow or porous structure. Particularly preferred particles and particles are described in U.S. Pat. Nos. 6,136,295, 5,985,309, 5,874,064, and 5,855, 913, and 6,858,199, the entirety of each of the foregoing patents is hereby incorporated herein by reference.

Other particles that can be useful in the claimed invention include those manufactured under the trademark PULMOSPHERES, developed by Nektar Therapeutics.

The method of the invention results in good to excellent emitted doses of the particle mass. In one embodiment, the emitted dose is at least 50%, preferably at least about 60%, more preferably at least about 70%. In a particularly preferred embodiment, the achieved emitted dose can be greater than about 80% such as at least about 85%.

The method can be readily achieved using an inhaler disclosed in the patent application filed in the United States Patent & Trademark Office on Oct. 10, 2002, having the title "Inhalation Device and Method" by Edwards et al., U.S. patent application Ser. No. 10/268,059, now U.S. Pat. No. 6,732,732, issued Oct. 11, 2004. Other inhalers that can be used include those described in PCT publication WO 02/083220, having the title "Inhalation Device and Method," by Edwards et al. published on Oct. 24, 2002. The contents of the applications are incorporated herein by reference in their entirety, together with their priority documents.

Alternative inhalers which can be used in the method are dry powder inhalers, including capsule loaded inhalers. Examples of suitable dry powder inhalers include but are not limited to the inhalers disclosed in U.S. Pat. Nos. 4,995,385 and 4,069,819, SPINHALER (Fisons, UK), ROTAHALER (GlaxoSmithKline, NC), FLOWCAPS (Hovione, Switzerland), INHALATOR (Boehringer-Ingelhein, Germany), AEROLIZER (Novartis, Switzerland), and the ECLIPSE (Aventis) and blister-based inhalers, such as DISKHALER (GSK, NC), and DISKUS (GSK, NC).

The selected low amounts of epinephrine particles used in the instant invention are 3.36 mg particle for delivery of lowest dose (300 ug epinephrine) which is an extremely low powder dose for inhalation. The combination of the dry powder aerosol with a respirable fraction (<4.7 μm) of 45% and the preferred inhaler maintained an unexpectedly high emitted dose. This translates into the ability to treat highly compromised patients and in particular, highly compromised children.

The Applicant compared the effectiveness of the instant invention against other available technologies. For example, the emitted dose data comparing the Diskhaler, Inhalator, Eclipse and C2S inhaler, shown in FIGS. 15 and 16, and FPF (%<3.3 microns) were preformed using 5.6 mg, corresponding to 500 μg active epinephrine which was used in the human clinical trial performed by Applicant. Inspiratory flow rates of 15, 30 and 60 L/min with a total volume of 2 liters were used for all the inhalers and then plotted as power (in watts) versus emitted dose. Power is a function of flowrate and resistance with each inhaler tested having a different resistance.

The formula used to calculate Power is:

$$\text{Power}=\text{Flowrate}^3\times\text{Resistance}^2$$

As indicated by the results, the comparison showed that at the low flow rate of 15 L/min in asthmatic patients in a compromised state (corresponding to less than 0.5 watts power for all inhalers tested) there is a fall off in emitted dose for all the inhalers except for the C2S inhaler, a preferred inhaler for the instant invention.

The same experiments were performed testing the lower epinephrine fill weight of 3.36 mg. This corresponds to 300 μg epinephrine at 15 L/min. The emitted dose was measured and the data shown in FIG. 14, demonstrating that less than about 5 mg particle mass were developed at less than about 20 L/min. More particularly, as shown, the emitted dose data for a 3.36 mg filled capsule is shown in FIG. 14. This compares favorably to the previous emitted dose data generated for the 5.6 mg fill weights.

Applicant employed two methods to obtain a measure of the emitted dose. A gravimetric analysis and a chemical analysis. Applicant performed the analysis according to the standard operating procedure (SOP) described below.

Applicant tested the particles under controlled environmental conditions of a room temperature of greater than about 18° C. but less than about 25° C. and a relative humidity of between about 20 and about 40. The equipment used in the Examples is shown in FIG. 17.

In performing the tests, a filled capsule was placed in the inhaler. Holding the inhaler vertically with the mouthpiece up, the capsule was punctured. The inhaler was placed in the inlet of the apparatus shown in FIG. 17, ensuring an airtight seal. Next the pump was activated using the flow controller. The flow rate selected was either 60 (±2) L/min for 2 seconds or a flow rate of 30 (±2) L/min for 4 seconds or a flow rate of 15 L/min for 8 seconds. In order to ensure that an airtight seal was attained, an equal flow rate was maintained in both meters (±2 L/min).

After performing the experiments and collecting the data, using the following formulae, the emitted dose was calculated.

$$ED=\frac{(m_{f1}-m_{f0})}{m_{fw}}\times 100$$

Where ED [%] is the emitted dose of the particles and $m_{f0}$ [mg] is the mass of the filter, $m_{f1}$ [mg] is the mass of the particle-laden filter and $m_{fw}$ [mg] is the actual or nominal fill weight.

Experiments in humans were conducted to evaluate the in vivo dose delivery characteristics of the delivery system of the instant invention over a wide range of inspiratory flow rates. The in vivo dose delivery of the pulmonary delivery system of the instant invention was characterized at a target peak inspiratory flow rate (PIFR) of 60 L/min (Dunbar et al., *Int. J. Pharm.* 245, 2002).

Twelve healthy volunteers participated in a single center, randomized, three period, cross-over study. Each volunteer performed the following three inhalation maneuvers: (i) a targeted peak inspiratory flow rate (PIFR) of 20 L/min, (ii) a deep comfortable inhalation, and (iii) a deep forced inhalation. Volunteers inhaled the radiolabeled placebo particles sitting upright, with their head and lungs posterial to the planar gamma camera. After a 5 s breath hold, the volunteers were instructed to exhale into a filter. Peak inspiratory flow rate (PIFR) and inhaled volume (V) were obtained during the inhalation of the dose using a spirometer (Koko Spirometer, Pulmonary Data Services Inc., Louisville, Colo.). Immediately following the radiolabeled dose, posterior scintigraphic images were taken using a planar gamma camera (DIACAM, Siemens Gammsonics, Inc., Hoffman Estates, Ill.). Four regions of interest were drawn around the left lung, right lung, stomach, and oropharynx (which included the upper part of the trachea). After subtracting the background activity, each region was corrected for tissue attenuation. The radioactivity in the pre-dosed capsule and the radioactivity remaining in the inhaler mouthpiece, inhaler body, post-dosed capsule, and exhalation filter were measured by scintigraphy using a high sensitivity NaI detector (Model 905, Perkin-Elmer, Oak Ridge, Tenn.). PIFR, emitted dose (ED), and lung deposition of the total dose were evaluated in this study.

The mean ED and lung deposition across all three inhalation maneuvers were 87 (4) % and 51 (10) %, respectively (sd in parentheses). The range of PIFRs obtained in this study was 12-86 L/min. The emitted dose and the lung deposition of the total dose as a function of PIFR are shown in the figures.

In conducting the human scintigraphy, 5 mg placebo was delivered via a simple, capsule based, passive dry powder inhaler such as the preferred inhaler described herein. The particles was radiolabeled with 99 mTc using a fluidized bed process (Dunbar et al., Int. J. Pharm., 245, 2002). Validation experiments were conducted to ensure the radiolabeling process did not significantly affect the aerodynamic particle size distribution (aPSD) of the emitted dose and the radioactive aPSD matched the mass aPSD. The mass aPSD of the unlabeled particles, the mass aPSD of the labeled particles, and the radioactive aPSD of the labeled particles were obtained using an 8-stage Andersen cascade impactor (Andersen Instruments, Smyrna, Ga.) with a USP induction port, shown in FIG. 11.

In a preferred embodiment, the inhaler comprises: a first casing portion; a cylindrical chamber, defined by a wall of circular cross-section, coupled to the first casing portion, the chamber having a proximal end and a distal end, the chamber comprising a ring circumferentially coupled to an inner surface of the chamber; and a second casing portion removably coupled to the first casing portion, the second casing portion comprising an inhalation portion disposed at the proximal end of the chamber when the first and the second casing portions are coupled, the inhalation portion comprising a hemispheric region defining a plurality of apertures configured to emit the mass.

As will be described in more detail below, an apparatus of the present invention is an inhaler that includes a chamber. In one embodiment, the chamber is configured to receive the receptacle containing the medicament. To improve the emptying of the receptacle and provide a higher reproducible emitted dose, the chamber includes a ring circumferentially coupled to an inner surface of the chamber. The ring is preferably disposed at approximately a midpoint of the chamber, or alternatively, adjacent the proximal end of the chamber. In proper use, air will exit the inhaler carrying a full dose of medicament in the form of a fine, dry particle mass.

The inhaler of the present invention is preferably configured with a means for puncturing the receptacle that improves puncturing performance, particularly with brittle receptacle material. The means for puncturing the receptacle of the present invention is preferably configured as a substantially U-shaped staple with two prongs, each prong having a sharp point and two cutting edges. In one embodiment of the present invention, each prong has a square cross-section, with the staple material being bent around a face so that the innermost part of the U-shaped staple is flat. In another embodiment of the present invention, the staple material is rotated 45 degrees so that it is bent around an edge so that the innermost part of the U-shaped staple is an edge. In such an embodiment, the end surface of each prong is an angled diamond-shaped surface.

The methods of the present invention use an inhaler to dispense particle by inhalation. As will be discussed in greater detail below, a user operates the device to puncture the receptacle to disperse particles in the chamber, and inhales the particles through the inhalation portion.

Figure 2:
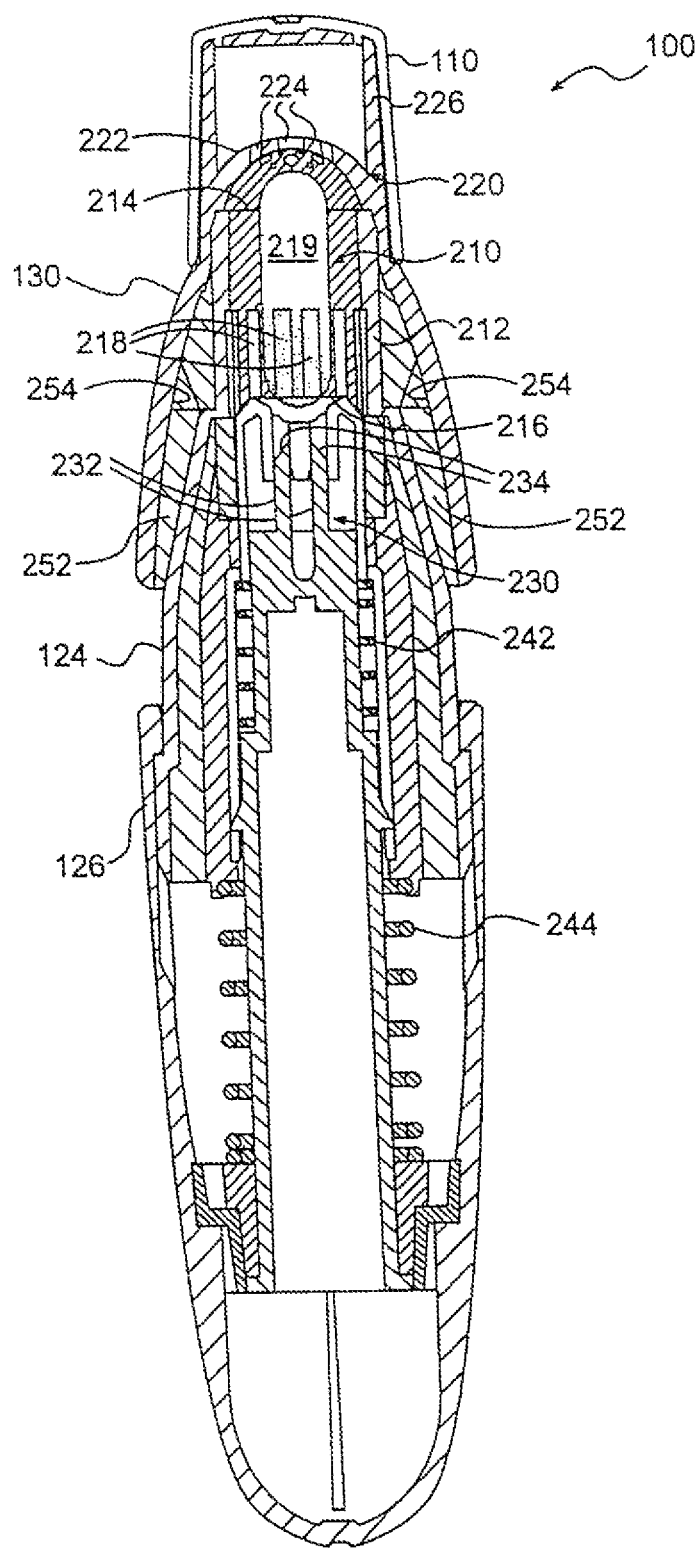
FIG. 2 is a cross-section of the device shown in FIG. 1 along line 2-2.

A front view of one embodiment of an inhalation device 100 of the present invention is shown in FIG. 1. The rear view of device 100 is substantially identical to the front view. Device 100 includes a first or lower casing portion 120 and a second or upper casing portion 130 removably coupled to first casing portion 120. Upper casing portion 130 and lower casing portion 120 include a flattened region 132 and 122, respectively, for ease of gripping the casing for use by a patient. Lower casing portion 120 preferably includes an outer casing 126 and an inner casing 124 movably received within outer casing 126. A removable cap 110 is provided at the user or inhalation end of the device. Preferred materials for device 100 include Food and Drug Administration (FDA) approved, USP tested plastics. Preferably, device 100 is manufactured using an injection molding process, the details of which would be readily apparent to one skilled in the art. FIG. 2 is a cross-section of device 100 shown in FIG. 1 along line 2-2. As shown in FIG. 2, device 100 includes an inhalation or emitter portion 220. Inhalation portion 220 comprises a hemispheric region 222 that defines a plurality of apertures 224. It should be understood that the present invention is not limited to a particular number of apertures 224, and can be configured such that at least one aperture 224 is provided. An inhalation piece 226 is provided to allow for inhalation of the medicament by a user.

Inhalation piece 226 can be configured as a mouth piece for inhalation through a user's mouth. Alternatively, inhalation piece 226 can be configured as a nose piece for inhalation through a user's nose.

Device 100 includes a cylindrical chamber 210 that is defined by a straight wall 212 of circular cross-section. Chamber 210 has a proximal end 214 and a distal end 216. A plurality of slits 218 are defined by wall 212, and are configured for introducing air into chamber 210 to disperse particles released from a capsule 219. It should be understood that the present invention is not limited to a particular number of slits 218, and can be configured such that at least one slit 218 is provided. Particles released from capsule 219 is dispersed in chamber 210 and inhaled through apertures 224 and inhalation piece 226 by the user.

In other embodiments of the invention, receptacles other than capsules are used, such as blisters and film covered container wells as is known in the art. In one embodiment, the volume of the receptacle is at least about 0.37 cm$^3$. In another embodiment, the volume of the receptacle is at least about 0.48 cm$^3$. In yet another embodiment, the receptacles have a volume of at least about 0.67 cm$^3$ or 0.95 cm$^3$. In one embodiment of the invention, the receptacle is a capsule designated with a capsule size 2, 1, 0, 00, or 000. Suitable capsules can be obtained, for example, from Shionogi (Rockville, Md.). Blisters can be obtained, for example, from Hueck Foils, (Wall, N.J.).

The receptacle encloses or stores particles, also referred to herein as powders. The receptacle is filled with particles in a manner known to one skilled in the art. For example, vacuum filling or tamping technologies may be used. Generally, filling the receptacle with powder can be carried out by methods known in the art.

Device 100 includes a means for puncturing 230 that is used to puncture capsule 219 to release particles contained therein into chamber 210. In the embodiment shown in FIG. 1, means for puncturing 230 is configured as a substantially U-shaped staple having two prongs 232. In this embodiment, each of prongs 232 is configured with a square cross-section 234, thereby providing a sharp point and two cutting edges. As discussed in more detail below, device 100 could alternatively be configured with the puncturing implement shown in FIGS. 7A through 7D. As can be readily appreciated by one skilled in the art, the present invention is not limited to use of a substantially U-shaped staple as the means for puncturing the capsule. Alternatively, one, or a plurality of, straight needle-like implements could be used. Preferably, the puncturing implement is configured to puncture at least two holes in the capsule.

Means for puncturing 230 is preferably configured to be movable between a non-puncturing position (as depicted in FIG. 1) and a puncturing position. In the puncturing position, prongs 232 pierce or puncture capsule 219 to make holes therein. In a preferred embodiment, a means for biasing is provided that biases the means for puncturing 230 in the non-puncturing position. In the embodiment shown in FIG. 2, the means for biasing is configured as a spring 242 that biases the substantially U-shaped staple in the non-puncturing position.

As noted with respect to FIG. 1, device 100 includes inner casing 124 and outer casing 126. As shown in FIG. 2, a spring 244 is disposed in lower casing portion 120 that biases inner casing 124 in an outward position. Upon compression of spring 244, inner casing 124 moves from the outward position to an inward position, thereby drawing lower casing portion 120 toward upper casing portion 130. Compression of spring 244 also causes compression of spring 242, thereby causing means for puncturing 230 to move to the puncturing position. Upon release of compression, springs 242 and 244 return to their biased state, thereby returning means for puncturing 230 to its non-puncturing position, and inner casing 124 to its outward position.

A pair of flanges 252 is disposed on first casing portion 120. A pair of grooves 254 is disposed on second casing portion 130 so that flanges 252 can be received within grooves 254 to thereby couple the first and second casing portions. Preferably, the first and second casing portions are coupled with a friction-fit engagement. A friction-fit engagement can be achieved using the groove and flange arrangement depicted in FIG. 2.

Other alternative configurations for a friction-fit engagement would be readily apparent to one skilled in the art.

Figure 3:
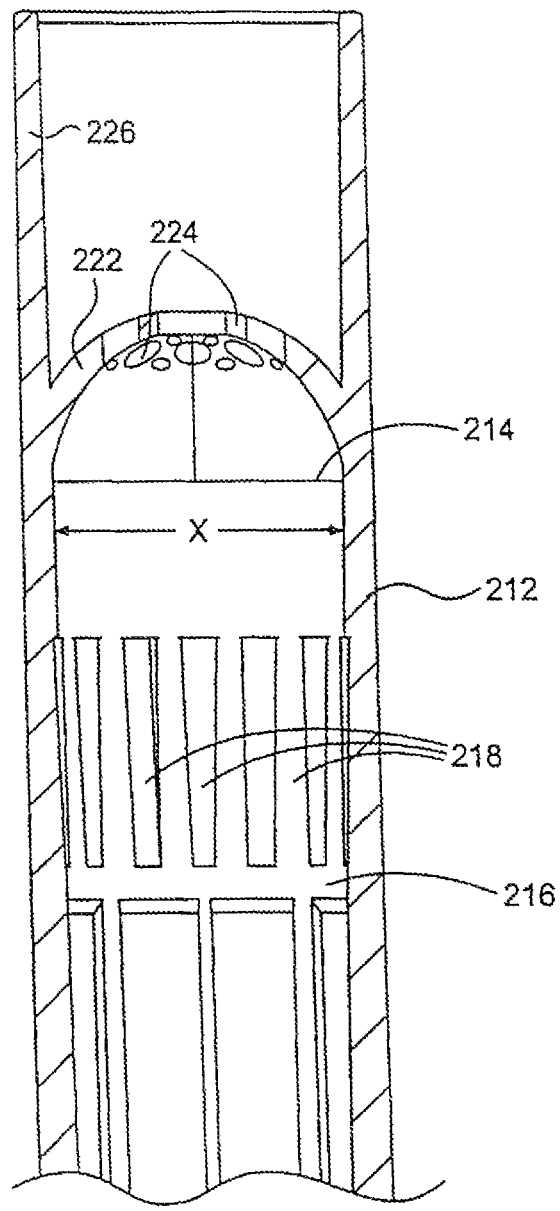
FIG. 3 is an enlarged partial cross-section of one embodiment of a dispersion chamber of the present invention.

FIG. 3 is an enlarged partial cross-section of one embodiment of chamber 210. In the embodiment shown in FIG. 3, chamber 210 does not contain a ring disposed on an inner surface, and an inner diameter of chamber 210 is depicted as "X". Such a configuration may be referred to herein as a "straight" chamber configuration.

Figure 4:
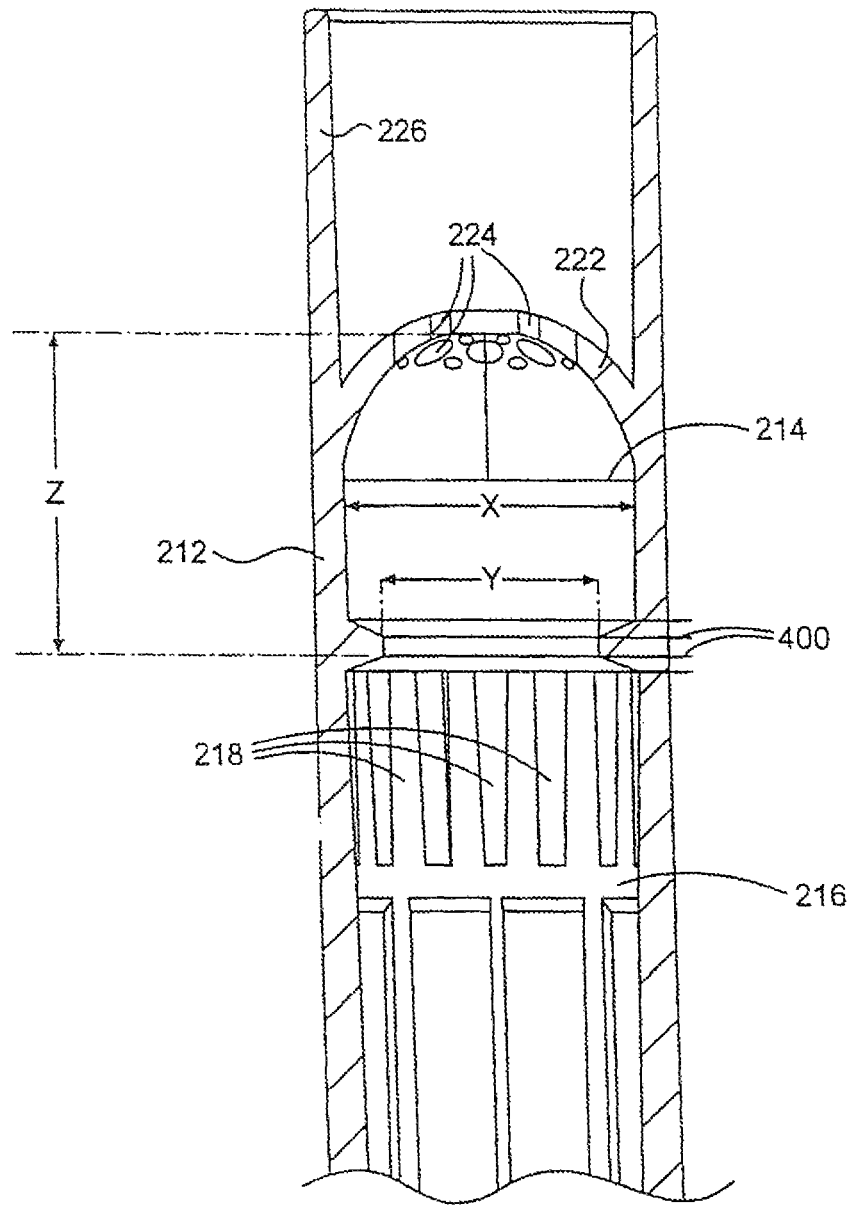
FIG. 4 is an enlarged partial cross-section of another embodiment of a dispersion chamber of the present invention showing one location for a ring in the dispersion chamber.

FIG. 4 is an enlarged partial cross-section of another embodiment of chamber 210. In the embodiment shown in FIG. 4, a ring 400 is circumferentially coupled to an inner surface of chamber 210. An inner diameter of ring 400 is depicted as "Y", and is less than inner diameter X of chamber 210. In the embodiment shown in FIG. 4, ring 400 is disposed at approximately a midpoint of chamber 210. Such a configuration may be referred to herein as a "low" ring position or "low" chamber configuration. As shown in FIG. 4, in the low ring position, ring 400 is disposed adjacent slits 218. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 4, diameter X is 0.47 in., diameter Y is 0.38 in., and distance Z is 0.49 in.

Figure 6:
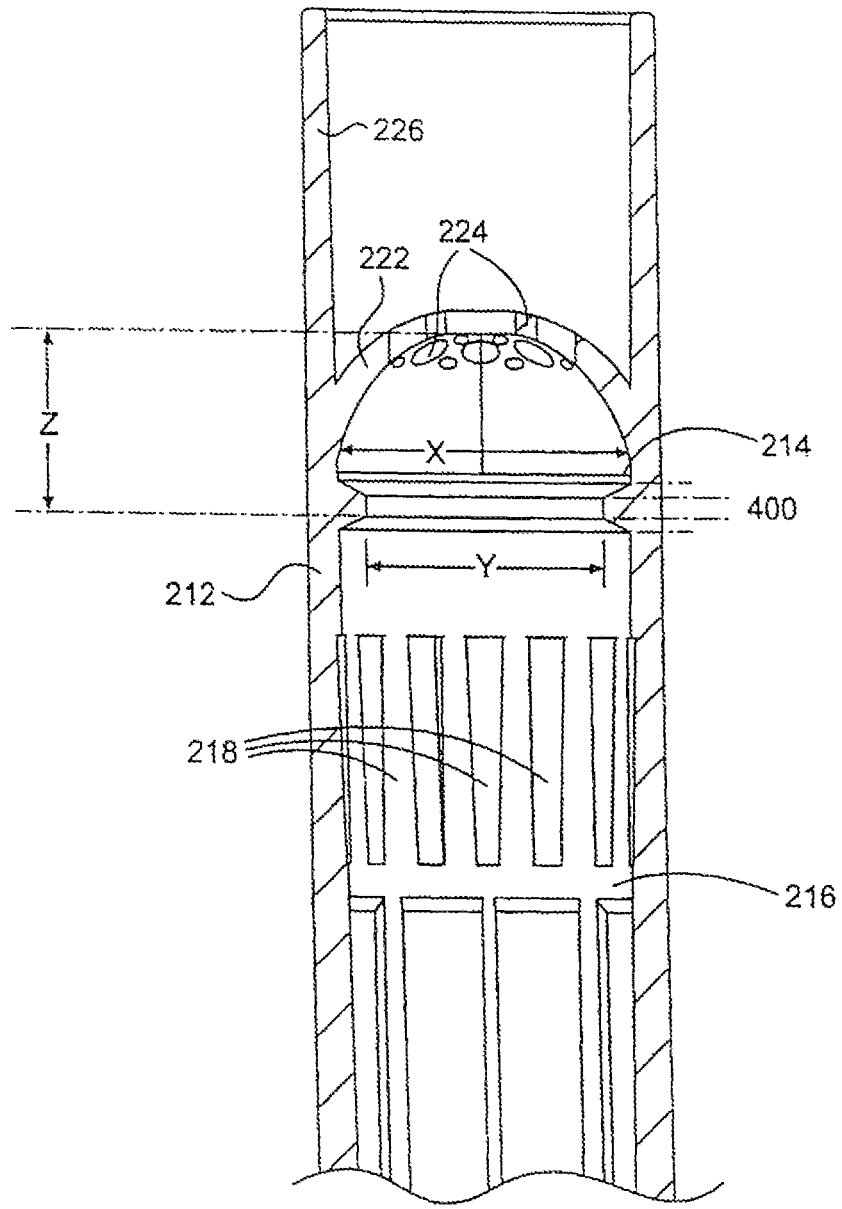
FIG. 6 is an enlarged partial cross-section of another embodiment of a dispersion chamber of the present invention showing another location for a ring in the dispersion chamber.
Figure 7A:
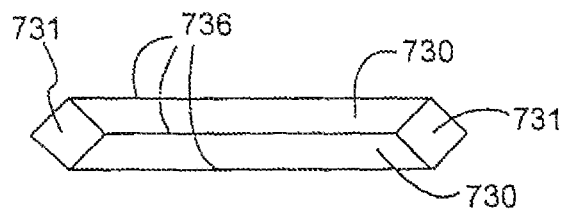
FIG. 7A is a top view of a preferred embodiment of a staple suitable for use with the device of the present invention.
Figure 7B:
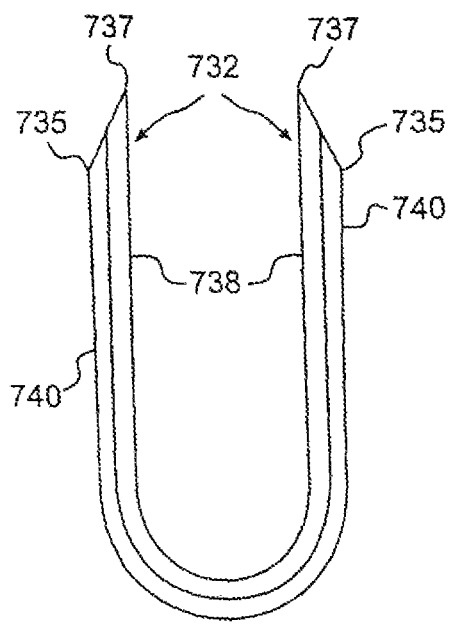
FIG. 7B is a front view of the embodiment shown in FIG. 7A.
Figure 7C:
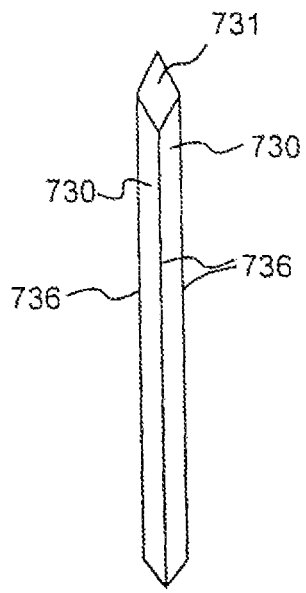
FIG. 7C is a side view of the embodiment shown in FIG. 7A.
Figure 7D:
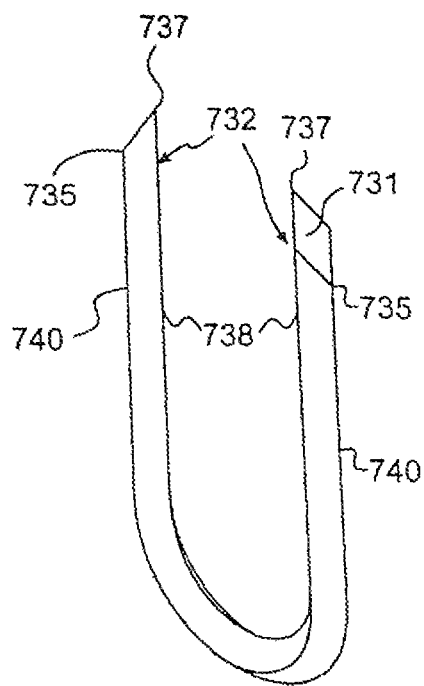
FIG. 7D is an isometric view of the embodiment shown in FIG. 7A.

FIG. 6 is an enlarged partial cross-section of another embodiment of chamber 210. In the embodiment shown in FIG. 6, ring 400 is circumferentially coupled to an inner surface of chamber 210. An inner diameter of ring 400 is depicted as "Y", and is less than inner diameter X of chamber 210. In the embodiment shown in FIG. 6, ring 400 is disposed adjacent the proximal end of chamber 210. Such a configuration may be referred to herein as a "high" ring position or a "high" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 6, diameter X is 0.47 in., diameter Y is 0.38 in., and distance Z is 0.29 in.

Figure 5:
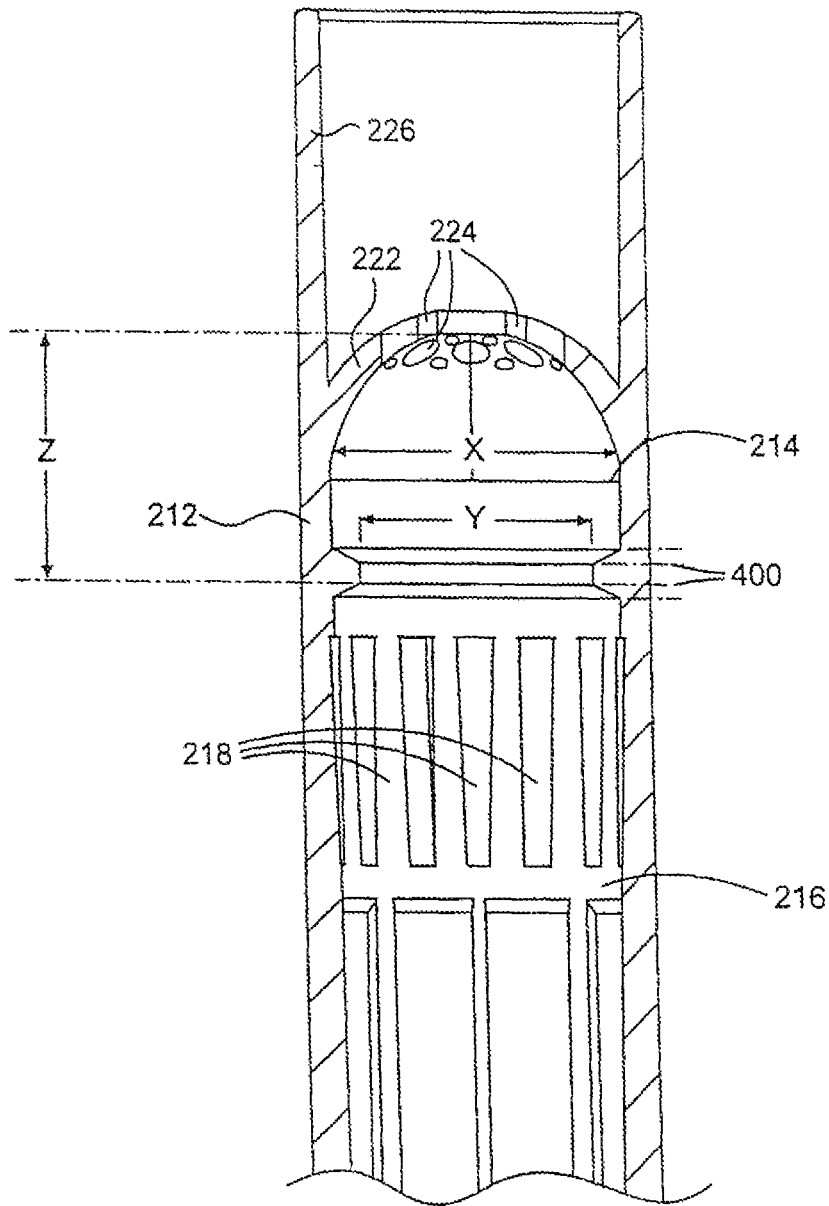
FIG. 5 is an enlarged partial cross-section of another embodiment of a dispersion chamber of the present invention showing another location for a ring in the dispersion chamber.

FIG. 5 is an enlarged partial cross-section of another embodiment of chamber 210. In the embodiment shown in FIG. 5, ring 400 is circumferentially coupled to an inner surface of chamber 210. An inner diameter of ring 400 is depicted as "Y", and is less than inner diameter X of chamber 210. In the embodiment shown in FIG. 5, ring 400 is disposed between the low ring position of FIG. 4 and the high ring position of FIG. 6.

Such a configuration may be referred to herein as a "mid" ring position or "mid" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 5, diameter X is 0.47 in., diameter Y is 0.38 in., and distance Z is 0.39 in.

In one embodiment of the present invention, ring 400 is integral with chamber 210. In such an embodiment, ring 400 and chamber 210 are formed as a unit, such as through an injection molding, extrusion or a casting process. In another embodiment of the present invention, ring 400 is attached to the inner surface of chamber 210 in a manner known to those skilled in the art, such as through the use of glue or other type of adhesive, or by using an attaching device such as a pin or screw, etc. Preferably, the casing of device 100 is made from a material that can be injection molded, such as a plastic material (preferably FDA approved, USP tested). As would be readily apparent to one skilled in the art, the material is preferably durable, easy to clean, and non-reactive with particles medicaments.

Figure 8:
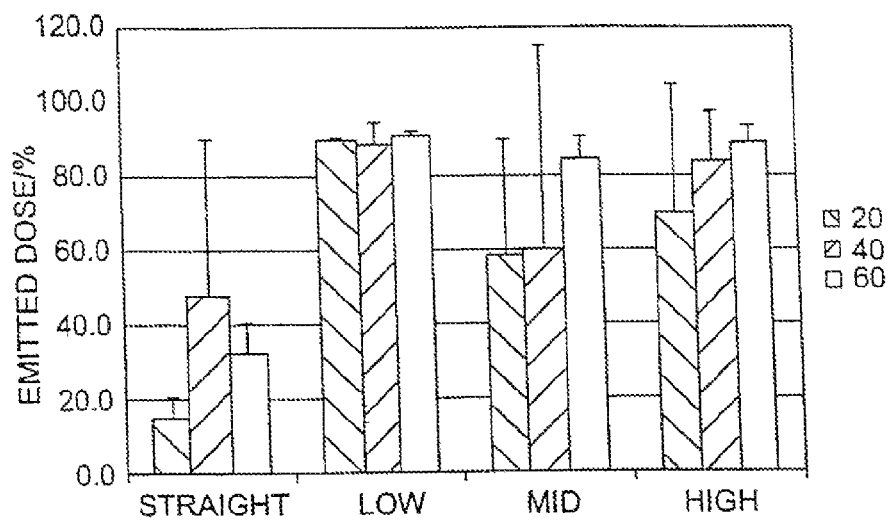
FIG. 8 is a bar graph illustrating emitted dose at flow rates of 20 L/min (left bar), 40 L/min (center bar), and 60 L/min (right bar) for four dispersion chamber configurations.

FIG. 8 is a bar graph illustrating emitted dose at flow rates of 20 L/min (left bar), 40 L/min (center bar), and 60 L/min (right bar) for a total volume of 2 L for four dispersion chamber configurations (standard deviations shown; sample size (n=3)). The flow rates were measured with a flow meter. The emitted dose measurement involved placing a capsule into four embodiments of the inhaler of the present invention for actuation into an emitted dose (ED) measurement apparatus. The ED apparatus included a powder filter and a filter holder. The particles collected by the ED apparatus were quantified by fluorescence spectrophotometry. The straight configuration is shown in FIG. 3; the low configuration is shown in FIG. 4; the mid configuration is shown in FIG. 5; and the high configuration is shown in FIG. 6. As can be seen from FIG. 8, each of the low, mid, and high configurations demonstrated a higher emitted dose at each of the three flow rates than the straight (no ring) configuration. Thus, the ring configuration of the present invention provides an improvement over conventional chamber designs without a ring. At each of the flow rates shown in FIG. 8, the low configuration produced a higher emitted dose and a lower standard deviation than the mid and high configurations.

Figure 9:
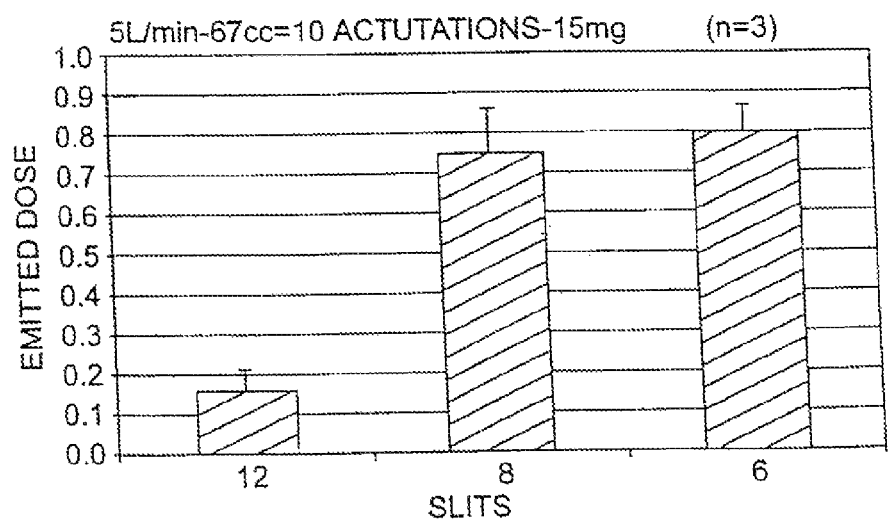
FIG. 9 is a bar graph illustrating emitted dose at low flow rates for devices with varying numbers of slits.

FIG. 9 is a bar graph illustrating emitted dose at low flow rates for devices with varying numbers of slits 218. A flow rate of less than about 15 L/min will be referred to herein as a "low flow rate." The measurements were taken at a flow rate of 5 L/min, with a volume of 67 cc and a 15 mg dosage. As show in FIG. 9, by decreasing the number of slits 218, the emitted dose increases so that the device of the present invention successfully delivers a high emitted dose at low flow rate over multiple (ten) actuations. Thus, the device of the present invention achieves a high emitted dose at low flow rates that is consistently reproducible with low standard deviation.

Figure 10:
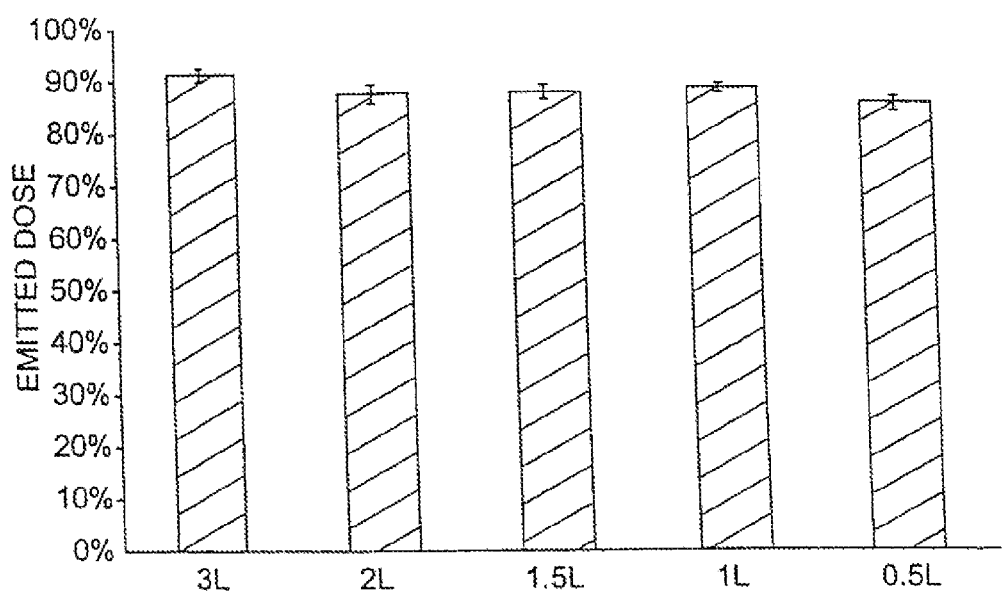
FIG. 10 is a bar graph illustrating the percentage emitted dose as a function of air volume.

Experiments were conducted to evaluate the emitted dose as a function of air volume drawn through the inhaler. The inhaler was operated at a constant flow rate of 30 L/min for a 5 mg dose. The volume of air through the inhaler was varied by varying the actuation time. Volumes of 0.5, 1.0, 1.5, 2.0 and 3.0 L were investigated. FIG. 10 shows the percentage emitted dose as a function of air volume (n=3, standard deviations shown).

The emitted dose remained constant across the range of volumes and was consistently reproducible with low standard deviation.

In the embodiments having the inner diameter X of chamber 210 of 0.47 in. and the inner diameter Y of ring 400 of 0.38 in., the ratio of the inner diameter of the ring to the inner diameter of the chamber is about 0.8. By modifying the inner diameters of the ring and the chamber, it is possible to optimize the emitted dose at varying flow rates. As reported in Annals of the ICRP, Human respiratory tract model for radiological protection, 24 (1-3), Elsevier Science, New York, 1994, the flow rate for a tidal breathing seated adult male is 300 mL/s (18 L/min) for a volume of 750 mL. In one embodiment of a device of the present invention optimized for low flow rates (less than about 15 L/min), inner diameter X of chamber 210 is 0.33 in. and inner diameter Y of ring 400 is 0.30 in. In such an embodiment, the ratio of the inner diameter of the ring to the inner diameter of the chamber is about 0.9. Preferably, the ratio of the inner diameter of the ring to the inner diameter of the chamber is about 0.9 or less.

The device of the present invention can also be optimized for varying dosage ranges. One way to do so is to vary the dimensions of chamber 210 to accommodate varying sizes of capsules. For example, a chamber having an inner diameter X of 0.33 in., inner diameter Y of 0.30 in., and distance Z of 0.57 in. can be used with size 2 and size 00 capsules. One skilled in the art can scale chamber 210 to accommodate varying capsule sizes, and to accommodate those capsule sizes at varying flow rates.

The present invention further encompasses optimizing the configuration of device chamber 210 in order to maintain a low resistance of 0.28 (cm $H_2O)^{1/2}$/L/min or less and to achieve an emitted dose of at least 50% when the receptacle contains a dose of up to 5 mg of particles and when the device is operated at a peak inspiratory flow rate of 20 L/min or less and/or at an inhalation volume of 0.75 L or less. Experiments were performed on various chamber configurations, using size 00 capsules filed with a 20 mg dose of standard test powder. The various configurations were tested for emitted dose (ED), using known methods described above, at peak inspiratory flow rates ranging from 15 L/min to 25 L/min and at inhalation volumes ranging from 0.25 L/min to 0.75 L/min. In addition, the dispersion of the particles was quantified by measuring the volume mean geometric diameter (VMGD) of the emitted particles, by employing a RODOS dry powder disperser (or equivalent technique) such that at about 1 Bar, particles of the dry powder emitted from the RODOS orifice with geometric diameters, as measured by a HELOS or other laser diffraction system, are less than about 1.5 times the geometric particle size as measured at 4 Bar. In addition, the resistance of each chamber was measured using methods that will be apparent to one of ordinary skill in the art.

The following dimensions of chamber 210 were varied in order to discover the optimal combination: mouthpiece hole area, mouthpiece hole number, chamber diameter (X in FIG. 4), ring diameter (Y in FIG. 4), vent area (the product of vent width, vent height, and vent number), and capsule hole area (the product of the hole area and the number of holes). Initially, it was discovered that it is always desirable to maximize the capsule hole area. Accordingly, the capsule hole area was fixed at 0.013 square inches. It should be understood that the present invention encompasses other capsule hole areas, especially when used with different sized capsules. It was also determined that the total area of the holes in the mouthpiece was an important factor but that the number of holes in the mouthpiece did not effect the results.

Next, 130 chambers were tested, each having a different combination of mouthpiece hole area, chamber diameter, ring diameter, and vent area. During the testing it was discovered that each of these dimensions have competing effects on the emitted dose, the volume mean geometric diameter, and the resistance of the chamber. For example, increasing the vent area has a positive impact on (i.e., decreases) resistance, but has a negative effect on (i.e., decreases) emitted dose and has a negative effect on (i.e., increases) volume mean geometric diameter. Other dimensions have similar competing effects. In addition, as discussed in detail below, the vent area and the chamber diameter have combinational effects on the properties of the chamber. Other combinations of dimensions have similar combinational effects.

Of the 130 chambers tested, three preferred embodiments of chambers were identified that achieved the desired characteristics. The pertinent dimensions of each of those chambers is described in Table 1.

TABLE 1

Aspects of Preferred Embodiments of Chambers

|  | Chamber F | Chamber H | Chamber I |
|---|---|---|---|
| Resistance (cm $H_2O)^{1/2}$/L/min | 0.27 | 0.22 | 0.19 |
| Mouthpiece Hole Area (sq. in.) | 0.020 | 0.022 | 0.022 |
| Chamber Diameter (in.) | 0.440 | 0.436 | 0.440 |
| Ring Diameter (in.) | 0.400 | 0.380 | 0.400 |
| Vent Area (sq. in.) | 0.014 | 0.020 | 0.024 |
| Vent Number (in.) | 3 | 4 | 5 |
| Vent Width (in.) | 0.020 | 0.025 | 0.020 |
| Vent Length (in.) | 0.236 | 0.195 | 0.236 |

Tables 2-4 summarize the emitted dose (ED) (in percent) and dispersion (volume mean geometric diameter (VMGD) in microns)) (with standard deviations in parentheses) achieved with each of these preferred embodiments of chambers, operated with a capsule having a dose of approximately 20 mg and at peak inspiratory flow rates from 15 L/min to 25 L/min and at inhalation volumes from 0.25 L to 0.75 L. The test particle mass, referred to herein as "standard test powder," was a placebo powder of 84.99 wt % maltodextran, 15 wt % leucine, and 0.01 wt % rhodamine. It had a VMGD of 12 µm measured using the RODOS at 1 bar and an aerodynamic size (volume mean aerodynamic diameter or VMAD) of 3 µm measured using an 8 stage Anderson Cascade Impactor. The goal emitted dose was at least 85%. The goal dispersion for the standard test powder was a VMGD of 11.8 µm or less, although it should be understood that this goal would vary depending on the type of powder used.

TABLE 2

Chamber F

| | Volume→ | | | | | |
|---|---|---|---|---|---|---|
| | 0.25 L | | 0.5 L | | 0.75 L | |
| Flow Rate | VMGD | ED | VMGD | ED | VMGD | ED |
| 15 L/min | 15.0 (0.8) | 67 (14) | 13.5 (0.8) | 87 (6) | 16.4 (1.6) | 93 (3) |
| 20 L/min | 10.2 (0.5) | 66 (9) | 9.3 (0.6) | 89 (4) | 9.0 (0.6) | 88 (10) |
| 25 L/min | 9.3 (0.6) | 77 (8) | 7.8 (0.3) | 91 (5) | 7.9 (0.5) | 93 (3) |

TABLE 3

Chamber H

| | Volume→ | | | | | |
|---|---|---|---|---|---|---|
| | 0.25 L | | 0.5 L | | 0.75 L | |
| Flow Rate | VMGD | ED | VMGD | ED | VMGD | ED |
| 15 L/min | 16.1 (0.8) | 57 (9) | 15.7 (0.7) | 78 (11) | 14.6 (1.1) | 90 (4) |
| 20 L/min | 12.0 (0.6) | 66 (9) | 10.4 (0.6) | 81. (7) | *10.2 (0.4)* | *89 (8)* |
| 25 L/min | 10.4 (0.6) | 75 (11) | *8.1 (0.3)* | *94 (4)* | *8.2 (0.3)* | *97 (1)* |

TABLE 4

Chamber I

| | Volume→ | | | | | |
|---|---|---|---|---|---|---|
| | 0.25 L | | 0.5 L | | 0.75 L | |
| Flow Rate | VMGD | ED | VMGD | ED | VMGD | ED |
| 15 L/min | 18.2 (0.7) | 49 (8) | 19.3 (1.3) | 69 (12) | 18.2 (1.9) | 79 (12) |
| 20 L/min | 13.4 (0.5) | 43 (13) | 12.7 (1.0) | 71 (10) | 12.5 (0.6) | 83 (9) |
| 25 L/min | 12.0 (0.4) | 65 (8) | *10.0 (0.4)* | *85 (7)* | *9.7 (0.3)* | *87 (9)* |

In Tables 2-4, the italicized print indicates peak inspiratory flow rates and inhalation volumes at which the chambers achieved both the goal of an emitted dose of at least 85% and a dispersion of a VMGD of 11.8 μm or less. As is apparent from Tables 2-4, these goals were achieved for peak inspiratory flow rates of 25 L/min or less and for inhalation volumes of 0.75 L or less. Moreover, the standard deviations were quite small for the emitted dose (on the order of approximately 10% or less) and for the VMGD (on the order of approximately 1.0 or less).

In addition, statistical analysis was used to extrapolate the results from these three chambers into ranges of variables that would consistently yield the desired emitted dose and volume mean geometric diameter. For example optimized combinations of chamber diameter, vent area, and mouthpiece hole area were determined. It should be apparent to one of ordinary skill in the art that optimization analysis could be performed for other variable combinations, and for other capsule sizes and powders, in order to optimize the design of the chambers.

Having done a thorough analysis, it has been determined that the present invention encompasses an optimized chamber, for a size 00 capsule, that has: at least one aperture has an aggregate area of 0.018 to 0.022 square inches; or a ring inner diameter of 0.380 to 0.400 inches; or a chamber inner diameter of 0.400 to 0.440 inches; or three to five vents; or a vent width of 0.020 to 0.025 inches; or a vent length of 0.195 to 0.236 inches; or a total vent area of 0.014 to 0.024 square inches, and that when used with a dose of approximately 20 mg of the standard test powder described above and operated at a peak inspiratory flow rate of 25 L/min or less and an inhalation volume of 0.75 L or less, the emitted dose of powder will be at least 85%, and the VMGD will be about 11.8 μm or less.

While the preferred embodiment described above relates to optimizing the design of a chamber to have a resistance of at most 0.28 (cm $H_2O)^{1/2}$/L/min and to provide an emitted dose of at least 85% when the dose of standard test powder is about 20 mg and when the device is operated at a peak inspiratory flow rate of 25 L/min or less and at an inhalation volume of 0.75 L or less it should be understood that the invention also encompasses optimizing the chamber to have any other combination of resistance and emitted dose, at any other combination of powder type, dose weight, peak inspiratory flow rate, and inhalation volume.

Turning now to FIGS. 7A through 7D, a preferred embodiment of a staple suitable for use in the present invention is shown. The staple preferably comprises a rectangular length of material that has four planar side surfaces 730. Each planar side surface intersects with two other planar side surfaces to create a total of four non-planar edges 736. The staple is preferably bent into a substantially U-shaped configuration, thereby having a rounded portion and two prongs 732. The prongs 732 terminate at two end surfaces 731. As best seen in FIGS. 7A, 7C and 7D, end surfaces 731 are diamond-shaped.

The diamond-shaped end surfaces are created by bending the material about a non-planar edge. This configuration is best shown in FIGS. 7B and 7D. As can be seen, each prong 732 has an inner surface 738 that comprises one of the non-planar edges and an outer surface 740 that comprises the opposite non-planar edge. The inner surface 738 of each prong 732 terminates at the uppermost portion 737 of the diamond-shaped end surface, thereby creating a cutting edge for the prong. The outer surface 740 of the prong 732 terminates at the lowermost portion 735 of the diamond-shaped end surface.

Another embodiment of a staple suitable for use in the present invention comprises a rectangular length of material that has four planar side surfaces. Each planar side surface intersects with two other planar side surfaces to create a total of four non-planar edges. The staple is preferably bent into a substantially U-shaped configuration, thereby having a rounded portion and two prongs.

The holes formed by this staple have the appearance of being cut with a sharp edge. In addition, the material removed to create the hole is peeled back and remains well attached to the capsule; thereby preventing the capsule material from being inhaled by the user when the medicament is being dispensed.

In addition to improved puncturing performance, drug delivery from capsules punctured with the staple depicted in FIGS. 7A-7D is greatly improved. The Emitted Dose (ED)

and Fine Particle Fraction (FPF) of a test powder was measured at both 20 and 60 Liters per minute (LPM). In all cases, the aerosol emitted from capsules punctured with the diamond section staple of FIGS. 7A-7D was improved over a conventional circular stock staple. Most significantly, the FPF of powder delivered at 20 liters per minute was improved almost to the level of the FPF at 60 liters per minute.

The present invention also relates to a method for dispensing medicaments to a user through the various embodiments of the disclosed inhalation device. In such a method, a receptacle containing the medicament, e.g., a capsule 219, is placed or formed into cylindrical chamber 210. When the user compresses the inhalation device, staple 230 is moved toward capsule 219 thereby puncturing capsule 219 to cause the release of particles masses into chamber 210. After release into the chamber, the powder is then inhaled by the user through apertures 224 and inhalation piece 226. As noted, inhalation piece 226, can be configured as either a mouth piece or a nose piece.

For subsequent uses, the user merely replaces emptied capsule 219 with another capsule 219 that contains a new supply of medicament. Alternatively, medicament is injected into a permanent receptacle that is formed into chamber 210.

EXEMPLIFICATION

Example 1

Particles containing epinephrine made in accordance with the method described in U.S. Application No. 60/425,349, which is incorporated herein by reference, were used.

Example 2

Applicant employed two methods to obtain a measure of the emitted dose. A gravimetric analysis and a chemical analysis. This example is a standard operating procedure (SOP) describing the method for obtaining the emitted dose using gravimetric analysis. This procedure relates to the release and stability testing of Applicant's products.

Unless otherwise indicated the following equipment, supplies, reagents and materials were used for both the Gravimetric analysis and the chemical analysis.

- 47 mm filter holder (e.g. BGI, Inc., Waltham, Mass.)
- Filter holder stand
- Flow meter (e.g. Model 32915-70 or equivalent, Cole-Parmer, Vernon Hills, Ill.)
- Flow controller (e.g. Model TPK, Erweka USA, Inc, Milford, Conn.)
- Vacuum pump (e.g. Model 1023-101Q-G608X, Gast MFG. CORP., Benton Harbor, Mich.)
- Silicon Vacuum tubing with inner diameter (ID) equal to 8±0.5 mm, outer diameter (OD) equal to 14±0.5 mm, and length equal to 50±10 cm (e.g. Peroxide-Cured Silicon tubing, Cole-Parmer, Vernon Hills, Ill.)
- Brass tubing connector with ID≥8 mm (e.g. Barbed fitting, Cole-Parmer, Vernon Hills, Ill.)

Additionally for the Gravimetric analysis, Applicant also used:

- 47 mm glass-fiber filters (A/E 47 mm (Pall Gelman No. 61631))
- Microbalance (capable of weighing 0.001 mg)
- Solvents include 100% methanol; 70/30% v/v ethanol/water; 70/30% v/v ethanol/0.1 M ammonium bicarbonate.

Under controlled environmental conditions of a room temperature of greater than about 18° C. but less than about 25° C. and a relative humidity of between about 20 and about 40%, Applicant prepared the apparatus. Using the solvents listed above, Applicant rinsed the individual components of the filter holder with the cleaning solvent and then with methanol and allowed them to dry. Applicant ensured that the filter holder was completely dry before beginning the analysis. The filter was then weighed on a microbalance and its mass was recorded to the nearest μg. The filter was placed in the filter holder with the rough side facing up. After attaching a flow meter to the inlet of the filter holder, Applicant adjusted the air flow rate using the needle valve on the flow controller. The flow rate selected was either 60 (±2) L/min for a duration of 2 seconds or a flow rate of 30 (±2) L/min for a duration of 4 seconds. In order to ensure that an airtight seal was attained, Applicant maintained an equal flow rate in both flow meters (±2 L/min). When an equal air flow rate was not obtained in both flow meters, Applicant (a) inspected the connections between apparatus components (b) disassembled the apparatus and (c) inspected the integrity of the connections. Placing an empty capsule into the inhaler, Applicant then attached the inhaler to the filter holder inlet, ensuring an airtight seal was obtained. The air flow rate was adjusted as mentioned above using the needle valve on the flow controller. The air flow rate was recorded to two significant figures. The empty capsule was then removed from the inhaler.

After the apparatus was prepared, Applicant then prepared the inhaler. For each run to measure the emitted dose, a new inhaler was used. A filled capsule was placed in the inhaler. Holding the inhaler vertically with the mouthpiece up, the capsule was punctured. The inhaler was placed in the inlet, ensuring an airtight seal. Next the pump was activated using the flow controller for a duration as defined above.

After the activation, Applicant cleaned the inhaler and unit dose sampling apparatus. The inhaler was carefully disassembled and the capsule was discarded into the appropriate waste container. The individual components were rinsed with methanol into a solvent collection container. Thereafter the filter holder was carefully dissembled. Using a microbalance, the powder-laden filter was weighed and its mass recorded to the nearest μg. The filter was discarded into the appropriate waste container. The individual components of the unit dose sampling apparatus were rinsed with cleaning solvent and then with methanol into a solvent collection container and allowed to dry.

Using the following formulae, Applicant calculated the emitted dose.

$$ED = \frac{(m_{f1} - m_{f0})}{m_{fw}} \times 100$$

Where ED [%] is the emitted dose of the particle and $m_{f0}$ [mg] is the mass of the filter, $m_{f1}$ [mg] is the mass of the powder-laden filter and $m_{fw}$ [mg] is the actual or nominal fill weight.

Applicant reported the emitted dose results (ED) as a percent based on the actual or nominal fill weight to three significant figures (xx.x %).

Example 3

Another procedure followed for obtaining the emitted dose was a chemical analysis. As with the Example above, the following was used:

- 47 mm filter holder (e.g. BGI, Inc., Waltham, Mass.)
- Filter holder stand

Flow meter (e.g. Model 32915-70 or equivalent, Cole-Parmer, Vernon Hills, Ill.)

Flow controller (e.g. Model TPK, Erweka USA, Inc, Milford, Conn.)

Vacuum pump (e.g. Model 1023-101Q-G608X, Gast MFG. CORP., Benton Harbor, Mich.)

Silicon Vacuum tubing with inner diameter (ID) equal to 8±0.5 mm, outer diameter (OD) equal to 14±0.5 mm, and length equal to 50±10 cm (e.g. Peroxide-Cured Silicon tubing, Cole-Parmer, Vernon Hills, Ill.)

Brass tubing connector with ID≥8 mm (e.g. Barbed fitting, Cole-Parmer, Vernon Hills, Ill.).

However for the chemical analysis, the following cleaning solvents, dissolving solvents and filters were used on the various parts of the apparatus.

| Cleaning solvent | Dissolving solvent | Filter |
| --- | --- | --- |
| 100% methanol | 100% HPLC grade methanol | A/E 47 mm (Pall Gelman No. 61631) |
| 70/30% v/v ethanol/water | 100% HPLC grade methanol | A/E 47 mm (Pall Gelman No. 61631) |
| 70/30% v/v ethanol/0.1M ammonium bicarbonate | 25 mM potassium phosphate 0.1% tween 80 pH 7.0 | MFMB 47 mm, 1.2 μm (Whatman) |
| 70/30% v/v ethanol/0.1M ammonium bicarbonate | 0.01N HCl | 47 mm, 1.2 μm (Corning) |
| 70/30% v/v ethanol/water | 92% methanol; 8% 0.01N HCl | A/E 47 mm (Pall Gelman No. 61631) |
| 70/30% v/v ethanol/0.1M ammonium bicarbonate | 70/30% v/v 0.05 HCl:MeOH | A/E 47 mm (Pall Gelman No. 61631) |

Other equipment included standard volumetric flasks, transfer pipettes, latex or butyl gloves (nitrile gloves should not be used).

As with Example 2 above, for pre- and post-analysis the environment was controlled. Under conditions of a room temperature of greater than about 18° C. but less than about 25° C. and a relative humidity of between about 20% and about 40%, Applicant prepared the apparatus. Using the solvents listed above, Applicant rinsed the individual components of the filter holder with the cleaning solvent and then with methanol and allowed them to dry. Applicant ensured that the filter holder was completely dry before beginning the analysis. In certain instances the apparatus was rinsed with water before rinsing with methanol. The filter was placed in the filter holder with the rough side facing up. The equipment was assembled. After attaching a flow meter to the inlet of the filter holder, Applicant adjusted the air flow rate using the needle valve on the flow controller. The flow rate selected was either 60 (±2) L/min for a duration of 2 seconds or a flow rate of 30 (±2) L/min for a duration of 4 seconds. In order to ensure that an airtight seal was attained, Applicant maintained an equal flow rate in both flow meters (±2 L/min). When an equal air flow rate was not obtained in both flow meters, Applicant (a) inspected the connections between apparatus components (b) disassembled the apparatus and (c) inspected the integrity of the connections. Placing an empty capsule into the inhaler, Applicant then attached the inhaler to the filter holder inlet, ensuring an airtight seal was obtained. The air flow rate was adjusted as mentioned above using the needle valve on the flow controller. The air flow rate was recorded to two significant figures. The empty capsule was then removed from the inhaler.

After the apparatus was prepared, Applicant then prepared the inhaler. For each run to measure the emitted dose, a new inhaler was used. A filled capsule was placed in the inhaler. Holding the inhaler vertically with the mouthpiece up, Applicant punctured the capsule. The inhaler was placed in the inlet, ensuring an airtight seal. Next the pump was activated using the flow controller for a duration as defined above.

After the activation, Applicant cleaned the inhaler and unit dose sampling apparatus. The inhaler was carefully disassembled and the capsule was not discarded as in the Example above. Instead the capsule was inspected and observations were recorded. The individual inhaler components were rinsed including the capsule, with the sample solvent into a volumetric flask. It should be noted that the Applicant tapped and removed all particle from the capsule using a round-ended micro spatula then rinsed the spatula with the sample solvent into the volumetric flask. However, they did not add the capsule to the volumetric flask. The filter holder was disassembled and the individual components of the filter holder were rinsed, including the filter, with the sample solvent into a volumetric flask. In some instances, the Applicant placed the filter in the volumetric flask. Sample solutions were transferred to suitable containers, e.g., scintillation vials, for storage and chemical analysis. The filter holder components were rinsed with cleaning solvent and then with methanol into a solvent waste container and allowed to dry. In some instances, Applicant, first rinsed all components with cleaning solvent, followed by further rinsing with water and then methanol.

The calculations were performed as above.

Example 4

Applicant conducted experiments in humans to evaluate the in vivo dose delivery characteristics of the delivery system of the instant invention over a wide range of inspiratory flow rates. The in vivo dose delivery of the pulmonary delivery system of the instant invention was characterized at a target peak inspiratory flow rate (PIFR) of 60 L/min (Dunbar et al., *Int. J. Pharm.*, 245, 2002).

Twelve healthy volunteers participated in a single center, randomized, three period, cross-over study. Each volunteer performed the following three inhalation maneuvers: (i) a targeted peak inspiratory flow rate (PIFR) of 20 L/min, (ii) a deep comfortable inhalation, and (iii) a deep forced inhalation. Volunteers inhaled the radiolabeled placebo powder sitting upright, with their head and lungs posterial to the planar gamma camera. After a 5 s breath hold, the volunteers were instructed to exhale into a filter. Peak inspiratory flow rate (PIFR) and inhaled volume (V) were obtained during the inhalation of the dose using a spirometer (Koko Spirometer, Pulmonary Data Services Inc., Louisville, Colo.). Immediately following the radiolabeled dose, posterior scintigraphic images were taken using a planar gamma camera (DIACAM, Siemens Gammsonics, Inc., Hoffman Estates, Ill.). Four regions of interest were drawn around the left lung, right lung, stomach, and oropharynx (which included the upper part of the trachea). After subtracting the background activity, each region was corrected for tissue attenuation. The radioactivity in the pre-dosed capsule and the radioactivity remaining in the inhaler mouthpiece, inhaler body, post-dosed capsule, and exhalation filter were measured by scintigraphy using a high sensitivity NaI detector (Model 905, Perkin-Elmer, Oak Ridge, Tenn.). PIFR, emitted dose (ED), and lung deposition of the total dose were the response factors evaluated in this study.

Scintigraphy images from a single subject were taken. The mean ED and lung deposition across all three inhalation maneuvers were 87 (4) % and 51 (10) %, respectively (sd in parentheses). The range of PIFRs obtained in this study was 12-86 L/min. The ED and the lung deposition of the total dose as a function of PIFR or as a function of inhaled volume are shown in FIGS. 12 and 13 or 19 and 20, respectively.

Figure 11:
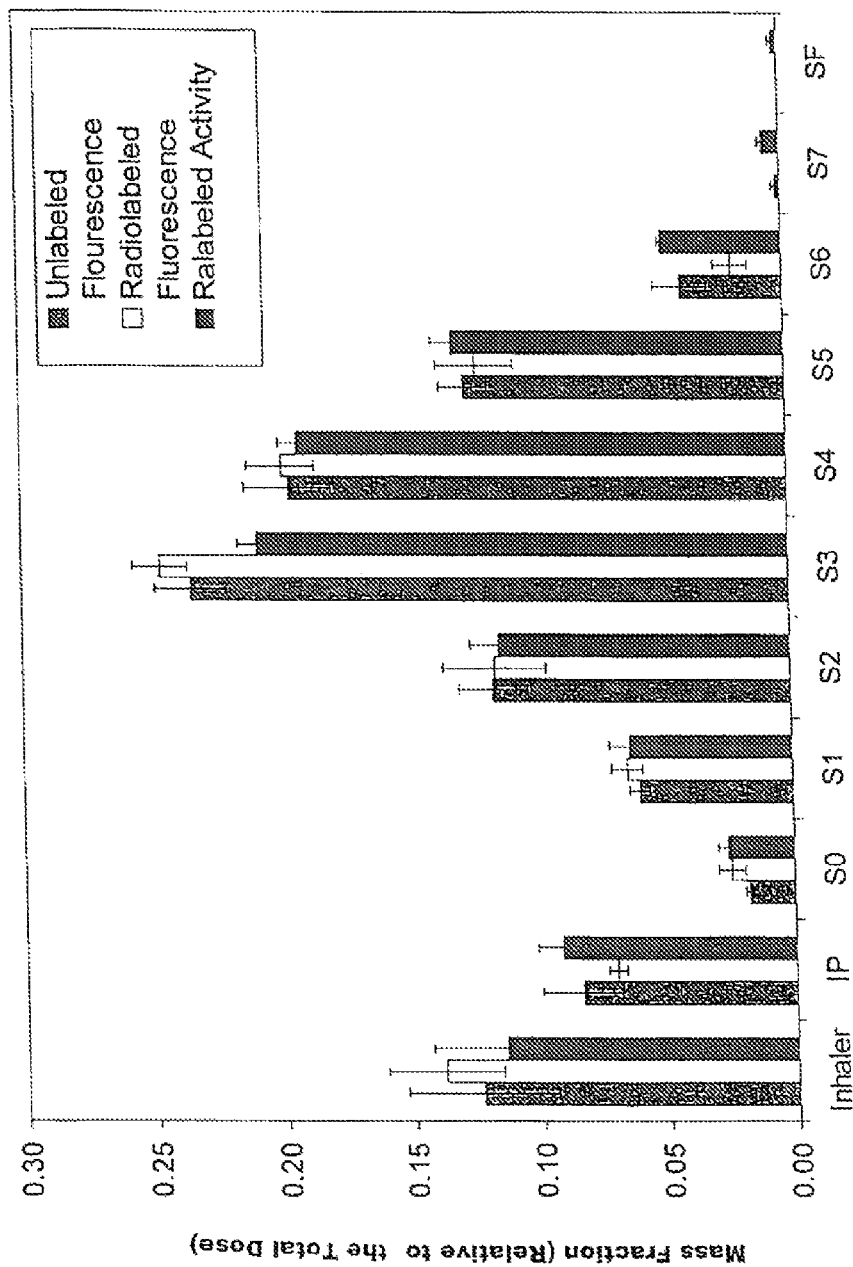
FIG. 11 shows radiolabeling validation data for the 5 mg placebo formulation.
Figure 12:
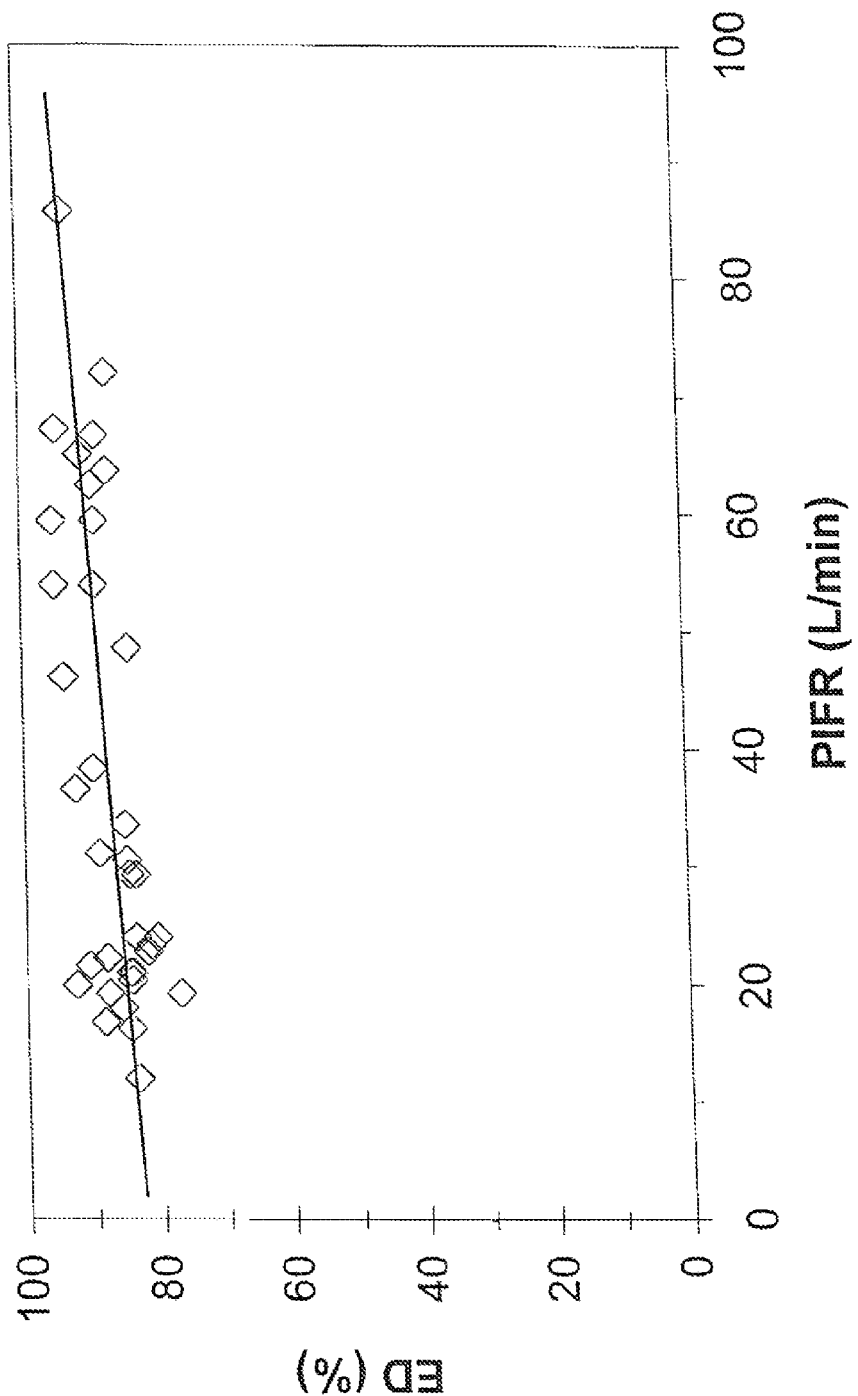
FIG. 12 shows emitted dose (ED) as a function of pulmonary inspiratory flow rate (PIFR)
Figure 13:
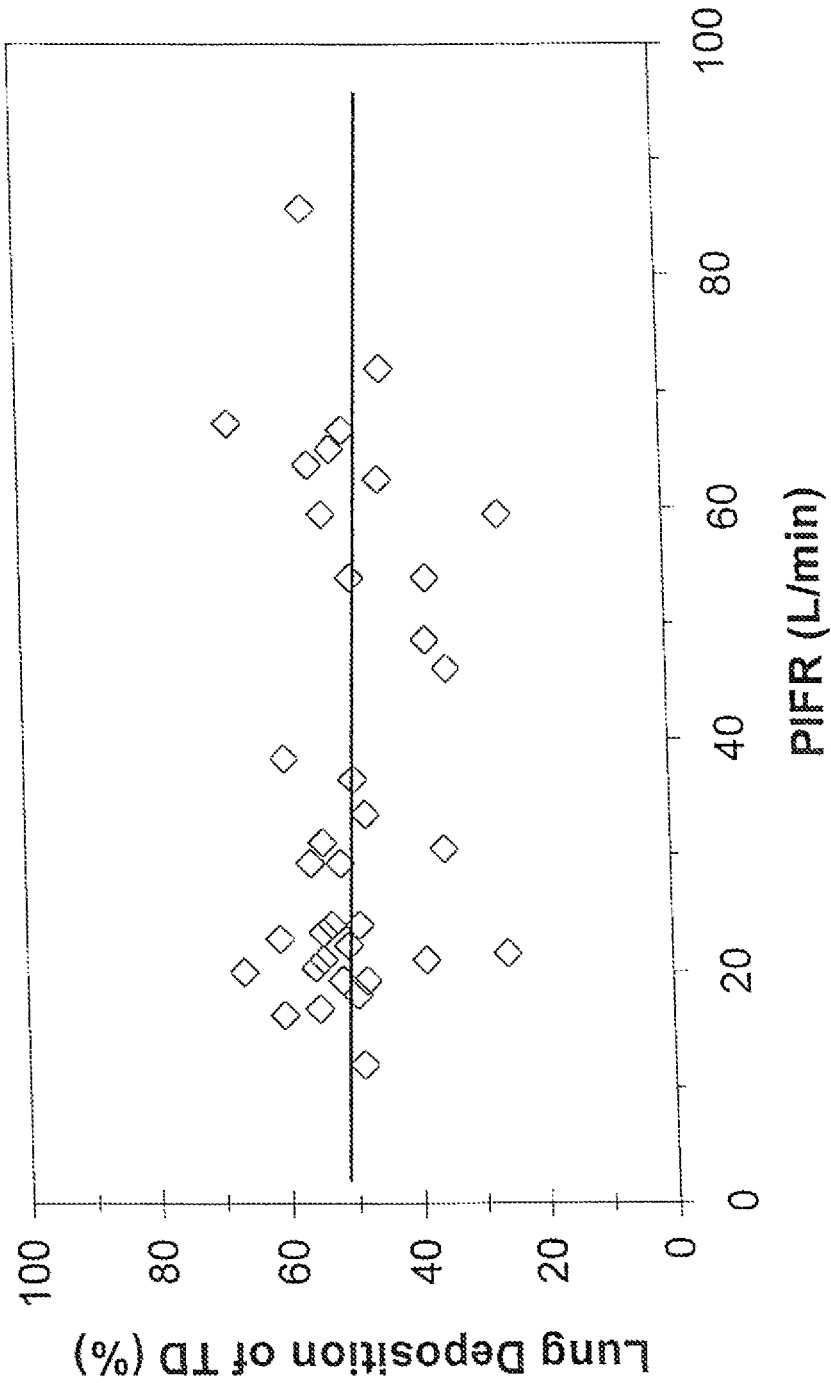
FIG. 13 shows the lung deposition of the total dose as a function of PIFR.
Figure 14:
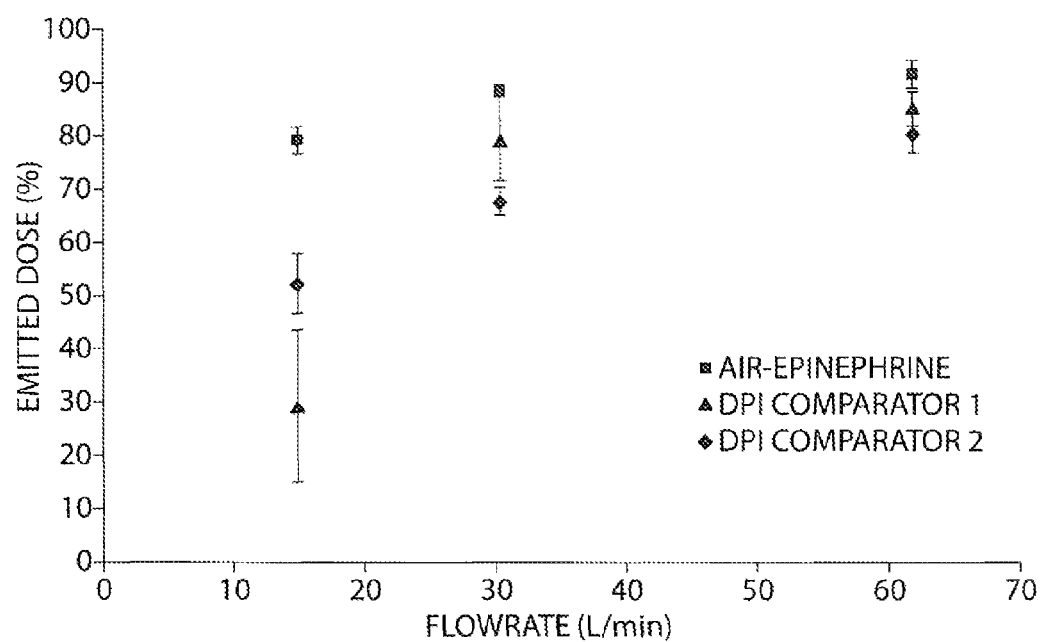
FIG. 14 shows AIR-epinephrine performance across inhalation flow rates.
Figure 15:
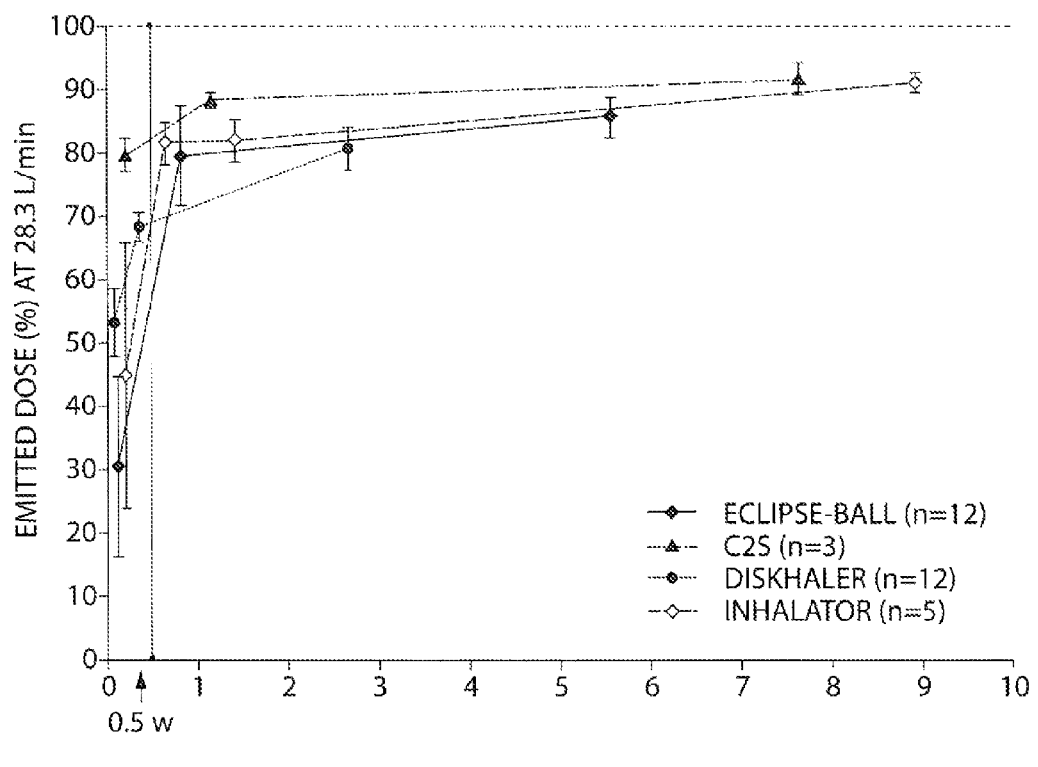
FIG. 15 shows the emitted dose versus power for different inhalers.
Figure 16:
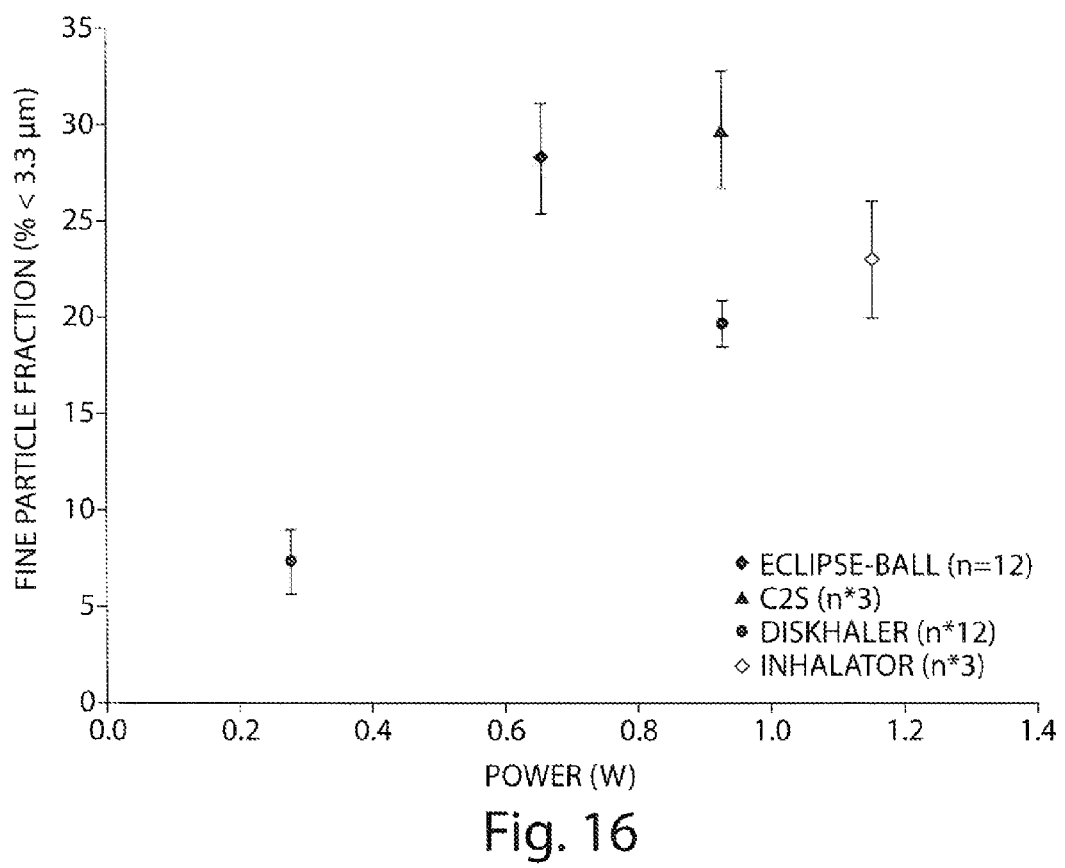
FIG. 16 shows the fine particle fraction (%<3.3 microns) versus power for different inhalers: The Eclipse, C2S (preferred inhaler of the instant invention), Diskhaler and Inhalator.
Figure 17:
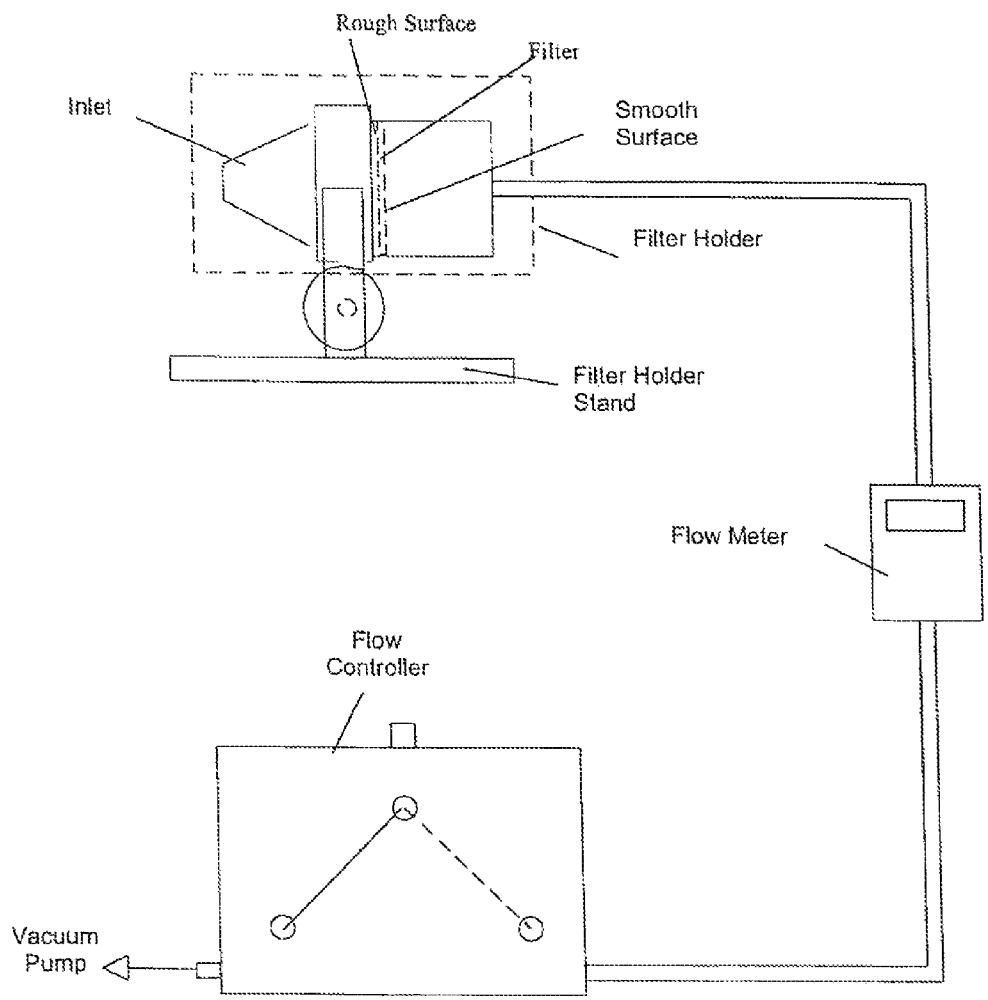
FIG. 17 shows the emitted dose apparatus.
Figure 18:
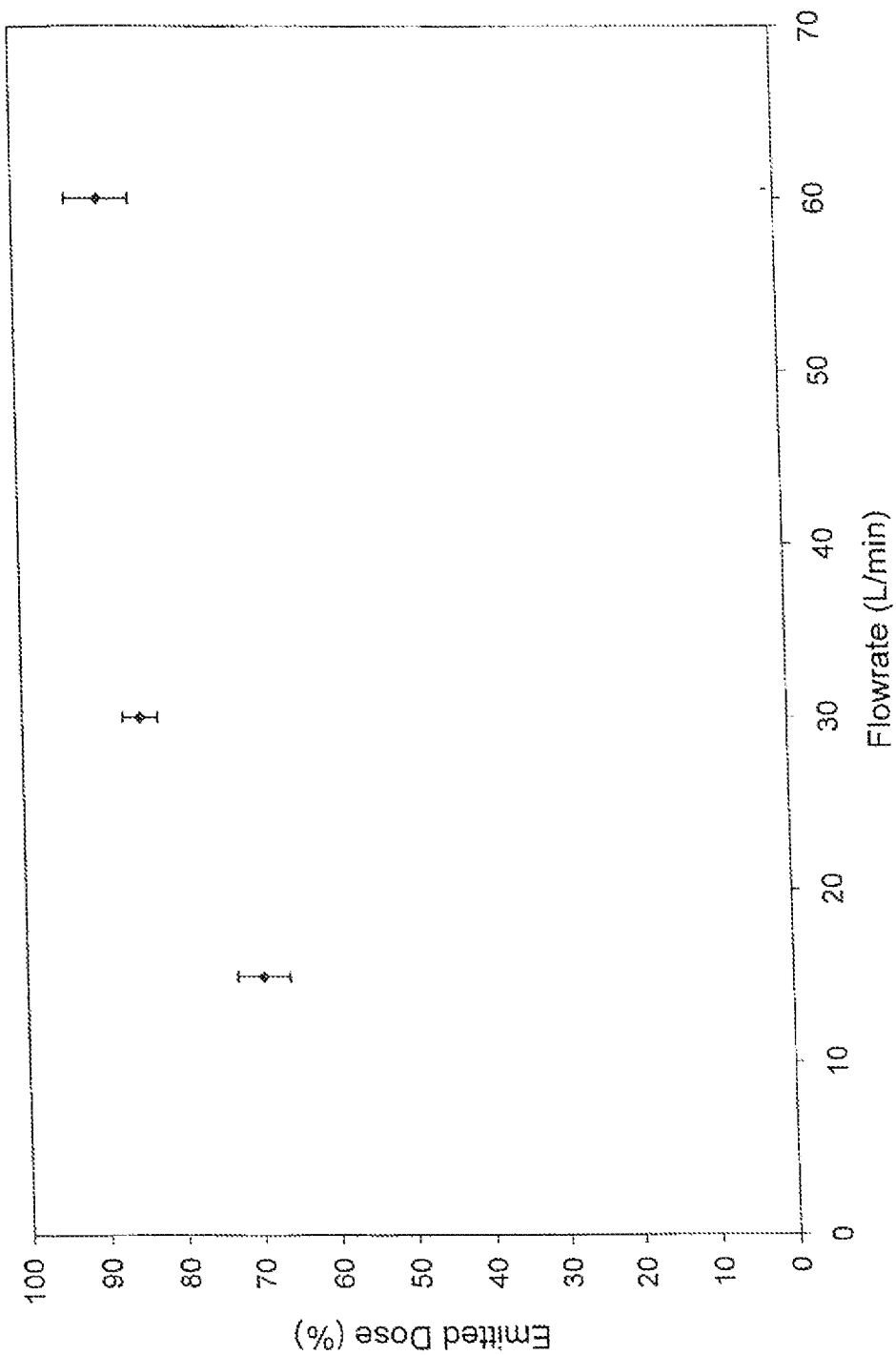
FIG. 18 shows the emitted dose as a function of flowrate.
Figure 19:
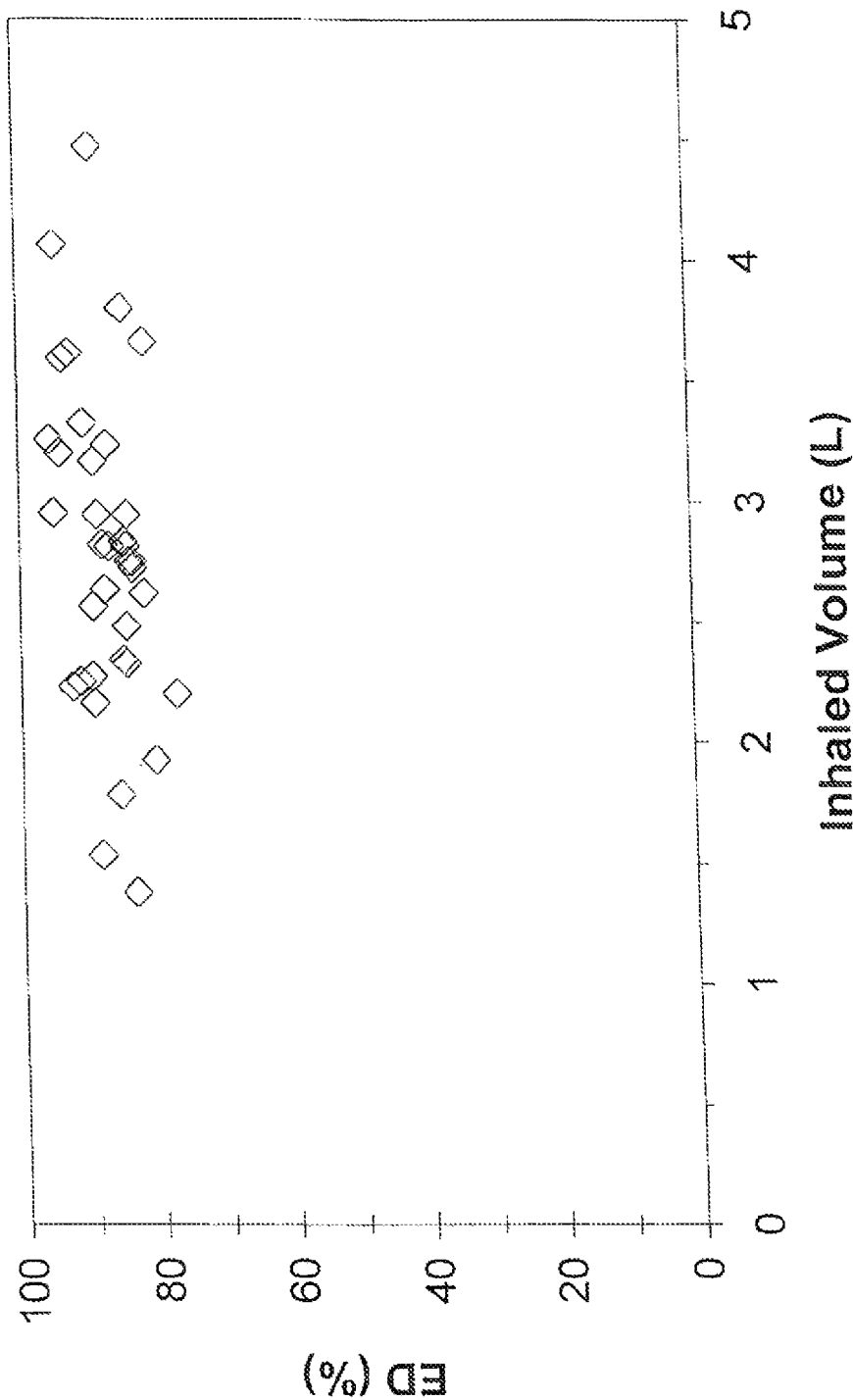
FIG. 19 shows the emitted dose as a function of inhaled volume.
Figure 20:
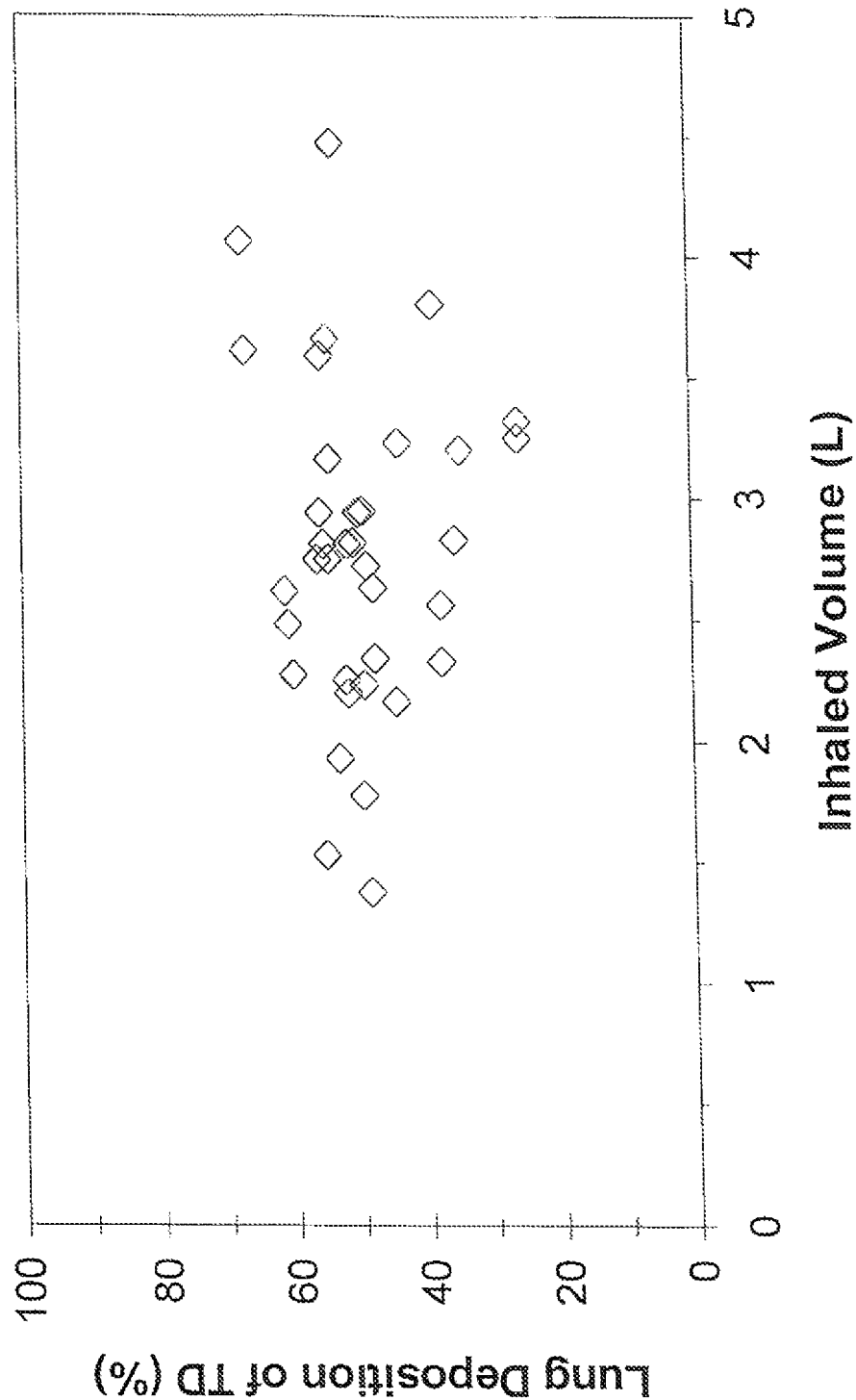
FIG. 20 shows the lung deposition as a function of inhaled volume.

Using 5 mg placebo, the powder was delivered via a simple, capsule based, passive dry powder inhaler such as the preferred inhaler described herein. The powder was radiolabeled with 99 mTc using a fluidized bed process (Dunbar et al., *Int. J. Pharm.*, 245, 2002). Validation experiments were conducted to ensure the radiolabeling process did not significantly affect the aerodynamic particle size distribution (aPSD) of the emitted dose and the radioactive aPSD matched the mass aPSD. The mass aPSD of the unlabeled powder, the mass aPSD of the labeled powder, and the radioactive aPSD of the labeled powder were obtained using an 8-stage Andersen cascade impactor (Andersen Instruments, Smyrna, Ga.) with a USP induction port, shown in FIG. 11.

Applicant observed that the in vivo dose delivery was characterized by high emitted doses and high lung deposition, with low variability. Lung deposition was independent of PIFR by analysis of variance across the wide range of inspiratory flow rates (p=0.498).

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

I claim:

1. A method of delivering an agent to the pulmonary system of a compromised patient, in a single breath-activated step, comprising administering a particle mass comprising an agent from an inhaler containing less than 5 milligrams of the mass, wherein at least about 50% of the mass in the inhaler is delivered to the pulmonary system of the patient.

2. A method of claim 1, wherein the inhaler contains less than 4 milligrams of the mass.

3. A method of claim 1, wherein the mass has a tap density of less than about 0.4 g/cm$^3$.

4. A method of claim 1, wherein the mass mean geometric diameter of the mass delivered to the pulmonary system of the patient is between about 3 microns and 15 microns.

5. A method of claim 1, wherein the mass mean geometric diameter of the mass delivered to the pulmonary system of the patient is between about 3 microns and 10 microns.

6. A method of claim 1, wherein the mass mean aerodynamic diameter of the mass delivered to the pulmonary system of the patient is between about 1 and 5 microns.

7. A method of claim 1, wherein the mass mean aerodynamic diameter of the mass delivered to the pulmonary system of the patient is between about 1 and 3 microns.

8. A method of claim 1, wherein greater than about 70% of the mass in the inhaler is delivered to the pulmonary system of the patient.

9. A method of claim 1, wherein the mass consists essentially of spray-dried particles.

10. A method of claim 1, wherein the inhaler comprises: a first casing portion; a cylindrical chamber, defined by a wall of circular cross-section, coupled to the first casing portion, the chamber having a proximal end and a distal end, the chamber comprising a ring circumferentially coupled to an inner surface of the chamber; and a second casing portion removably coupled to the first casing portion, the second casing portion comprising an inhalation portion disposed at the proximal end of the chamber when the first and the second casing portions are coupled, the inhalation portion comprising a hemispheric region defining a plurality of apertures configured to emit the mass.

11. A method of claim 10, wherein the ring is disposed at approximately a midpoint of the chamber.

12. A method of claim 10, wherein said inhaler further comprises a plurality of slits defined by said wall, said plurality of slits configured for introducing air into said chamber.

13. A method of claim 10, wherein the inhaler further comprises a movable puncturing tool, disposed in said first casing portion, for puncturing a receptacle containing the mass.

14. A method of claim 1, wherein the inhaler possesses a resistance of less than about 0.28 (cm H$_2$O)$^{1/2}$/L/min.

15. A method of claim 14, wherein the inhalation volume of the patient is less than about 1.0 L.

16. A method of claim 10, wherein the receptacle has a volume of less than about 0.67 cm$^3$.

17. A method of claim 10, wherein the receptacle has a volume of less than about 0.48 cm$^3$.

* * * * *